(12) United States Patent
Koide et al.

(10) Patent No.: US 11,340,164 B2
(45) Date of Patent: May 24, 2022

(54) FLUORESCENT METHOD TO QUANTIFY COPPER OR PLATINUM BASED ON CATALYSIS

(71) Applicant: University of Pittsburgh—Of the Commonwealth System of Higher Education, Pittsburgh, PA (US)

(72) Inventors: Kazunori Koide, Pittsburgh, PA (US); Melissa L. Campbell, Pittsburgh, PA (US); Dianne Pham, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 436 days.

(21) Appl. No.: 16/381,504

(22) Filed: Apr. 11, 2019

(65) Prior Publication Data
US 2019/0323964 A1    Oct. 24, 2019

Related U.S. Application Data

(60) Provisional application No. 62/656,067, filed on Apr. 11, 2018.

(51) Int. Cl.
*G01N 21/64* (2006.01)
*G01N 33/20* (2019.01)

(52) U.S. Cl.
CPC ......... *G01N 21/6428* (2013.01); *G01N 33/20* (2013.01); *G01N 21/643* (2013.01); *Y10T 436/16* (2015.01)

(58) Field of Classification Search
CPC .. G01N 21/64; G01N 21/6428; G01N 21/643; G01N 21/6486; G01N 33/20; Y10T 436/142222; Y10T 436/16; Y10T 436/19; Y10T 436/203332
USPC .. 436/63, 73, 74, 80, 84, 93, 103, 124, 131, 436/164, 166, 172; 422/82.05, 82.08
See application file for complete search history.

(56) References Cited

U.S. PATENT DOCUMENTS

| | | | | |
|---|---|---|---|---|
| 7,615,377 | B2 * | 11/2009 | Lippard | G01N 33/5308 422/534 |
| 2008/0274492 | A1 * | 11/2008 | Koide | C09B 11/08 435/29 |
| 2008/0275257 | A1 * | 11/2008 | Koide | C07D 311/82 549/391 |
| 2017/0276607 | A1 * | 9/2017 | Helal | G01N 33/582 |

OTHER PUBLICATIONS

Pham et al. ACS Central Science, vol. 6, pp. 1772-1788, Sep. 18, 2020.*

Aletras et al., "On the Mechanism of Action of the Antitumor Drugs cis-Platin (cis-DDP) and Its Second Gereneration Derivatives", Met. Based Drugs, 1995, pp. 153-185, vol. 2, No. 3.
Atwood et al., "Characterization of Copper Interactions with Alzheimer Amyloid Beta Peptides: Identification of an Attomolar-Affinity Copper Binding Site on Amyloid Beta-1-42", Journal of Neurochemistry, 2000, pp. 1219-1233, vol. 75.
Balamurugan et al., "A depropargylation-triggerd fluorescence "turn-on" probe for the detection of Pd2+ based on a bispropargylamine-rhodamine conjugate", Analyst, 2013, pp. 1564-1569, vol. 138.
Bellingham et al., "Copper Depletion Down-regulates Expression of the Alzheimer's Disease Amyloid-Beta Precursor Protein Gene", The Journal of Biological Chemistry, 2004, pp. 20378-20386, vol. 279, No. 19.
Bosch et al., "Anaytical methodolgies for the determination of cisplatin", Journal of Pharmaceutical and Biomedical Analysis, 2008, pp. 451-459, vol. 47.
Bu et al., "Rapid Analysis of Residual Palladium in Pharmaceutical Development Using a Catalysis-Based Fluorometric Method", Org. Process Res. Dev., 2013, pp. 108-113, vol. 17.
Bu et al., "Online sensing of palladium in flowing streams", Chem. Commun., 2017, pp. 720-723, vol. 53.
Cai et al., "Platinum(II)-Oligonucleotide Coordination Based Aptasensor for Simple and Selective Detection of Platinum Compounds", Anal. Chem., 2015, pp. 10542-10546, vol. 87.
Chae et al., "Fluorimetric Chemodosimetry. Mercury(II) and Silver(I) Indication in Water via Enhanced Fluorescence Signaling", J Am. Chern. Soc 1992, pp. 9704-9705, vol. 114.
Chen et el., "A facile naphthalene-based fluorescent 'turn-on' chemodosimeter for palladium ions in aqueous solution", Tetrahedron Letters, 2016, pp. 1192-1195, vol. 57.
Chen et al., "A Depropargylation-Triggered Spontaneous Cyclization Based Fluorescent "Turn-On" Chemodosimeter tor the Detection of Palladium Ions and Its Application in Live-Cell Imaging", J. RSC Adv., 2016, pp. 8380-8383, vol. 6.
Chen et al., "Highly sensitive and selective ESIPT-based fluorescent probes for detection of Pd+2 with large Stocks shifts", Dyes and Pigments, 2017, pp. 392-398, vol. 140.
Cheng et al., "Cu-Pybox catalyzed synthesis of 2,3-disubstituted imidazo[1,2-alpha] pyridines from 2-aminopyridines and propargyl alcohol derivatives", Tetrahedron, 2016, pp. 6866-6874, vol. 72.
Cherny et al., "Treatment with a Copper-Zinc Chelator Markedly and Rapidly Inhibits Beta-Amyloid Accumulation in Alzheimer's Disease Transgenic Mice", Neuron, 2001, pp. 665-676, vol. 30.
Cho et al., "Modern reaction-based indicator systems", Chem Soc Rev., 2009, pp. 1647-1662, vol. 38:6.
Cicchella et al., "Palladium and platinum concentration in soils from the Napoli metropolitan area, Italy: possible effects of catalytic exhausts", The Science of the Total Environment, 2003, pp. 121-131, vol. 308.
Colacot (Editor), "New Trends in Cross-Coupling Theory and Applications", Royal Society of Chemistry 2015, West Deptford, New Jersey, USA, pp. 1-12.
Collins et al., "A New Initiative on Precision Medicine", N Engl J Med., 2015, pp. 793-795, vol. 372:9.

(Continued)

*Primary Examiner* — Maureen Wallenhorst
(74) *Attorney, Agent, or Firm* — The Webb law Firm

(57) ABSTRACT

Methods of detecting platinum and copper in a test sample are provided. Kits for use in detecting platinum and copper in a test sample also are provided.

12 Claims, 17 Drawing Sheets

(56) References Cited

OTHER PUBLICATIONS

Corradini et al., "Fluorescent Chemosensor for Organic Guests and Copper (II) Ion Based on Dansyldiethylenetriamine-Modified Beta-Cyclodextrin", J. Org Chem, 1997, pp. 6283-6289, vol. 62.
Cotruvo, Jr. et al., "Synthetic fluorescent probes for studying copper in biological systems", Chemical Society Reviews, 2015, pp. 4400-4414, vol. 44.
Cracknell et al., "Bilirubin oxidase from Myrothecium verrucaria: X-ray determination of the complete crystal structure and a rational surface modifcation for enhanced electrocatalytic O2 reduction", Dalton Trans., 2011, pp. 6668-6675, vol. 40.
De Jongh et al., "Cisplatin Scheduling and Dosing Aspects", J. Clin. Oncol., 2001, pp. 1-104, vol. 19.
Dhoun et al., "Propargylated cyanostilbene based chemodosimeter for Pd2+ with application in biological fluids", Dyes and Pigments, 2017, pp. 361-367, vol. 143.
Di Pasqua et al., "Understanding how the platinum anticancer drug carboplatin works: From the bottle to the cell", Inorganica Chimica Acta, 2012, pp. 29-35, vol. 389.
Dodani et al., "Calcium-dependent copper redistributions in neuronal cells revealed by a fluorescent copper sensor and X-ray fluorescence microscopy", PNAS, 2011, pp. 5980-5985, vol. 108, No. 15.
Erythropel et al., "The Green ChemisTREE: 20 years after taking root with the 12 principles", Green Chem. 2018, pp. 1929-1961, vol. 20.
Garner et al. "Fluorescent method for platinum detection in buffers and serums for cancer medicine and occupational hazards", Chem. Commun, 2009, pp. 83-85.
Garner et al., "Studies of a fluorogenic probe for palladium and platinum leading to a palladium-specifc detection method", Chem. Commun., 2009, pp. 86-88.
Gurney, "How to calculate the dose of chemotherapy", British Journal of Cancer, 2002, pp. 1297-1302, vol. 86.
Handa et al., "Sustainable Fe-ppm Pd nanoparticle catalysis of Suzuki-Miyaura cross-couplings in water", Science, 2015, pp. 1087-1090, vol. 349, Issue 6252.
Hirayama et al., "Near-infrared fluorescent sensor for in vivo copper imaging in a murine Wilson disease model", PNAS, 2012, pp. 2228-2233, vol. 109, No. 7.
Huang et al., "Trialkyl Methanetricarboxylate as Dialkyl Malonate Surrogate in Copper-Catalyzed Enantioselective Propargylic Substitution", Org. Lett., 2015, pp. 4894-4897, vol. 17.
Huo et al., "A novel alkyne compound as a Pd(II) fluorescent probe in aqueous medium and its bioimaging", Sensors and Actuators B: Chemical, 2017, pp. 429-434, vol. 243.
Ingle, Jr. et al., "Spectrochemical Analysis", Prentice Hall, Upper Saddle River, New Jersey, USA, 1988, pp. 1-31.
Johnstone et al., "The Next Generation of Platinum Drugs: Targeted Pt(II) Agents, Nanoparticle Delivery, and Pt(IV) Prodrugs", Chem Rev., 2016, pp. 3436-3486, vol. 116:5.
Jun et al., "Turn-on" fluorescent sensing with "reactive" probes, Chem. Commun., 2011, pp. 7583-7601, vol. 47.
Kim et al., "Rhodamine Triazole-Based Fluorescent Probe for the Detection of Pt2+", Organic Letters, 2010, pp. 5342-5345, vol. 12, No. 22.
Koide et al., "Scalable and Concise Synthesis of Dichlorofluorescein Derivatives Displaying Tissue Permeation in Live Zebrafish Embryos", Chembiochem., 2008, pp. 214-218, vol. 9:2.
Koide et al., "A competive and reversible deactivation approach to catalysis-based quantitative assays", Nat. Commun., 2016, pp. 10691-10698, vol. 7.
Kovacs et al., "Catalytic Hydrolysis of Esters of 2-Hydroxypyridine Derivatives for Cu2+ Detection", Inorg. Chem., 2008, pp. 1880-1882, vol. 47.
Kumar et al., "Highly Selective Fluorescence Turn-on Chemodosimeter Based on Rhodamine for Nanomolar Detection of Copper Ions", Organic Letters, 2012, pp. 406-409, vol. 14, No. 1.

Lavoie et al., "Challenging nickel-catalysed amine arylations enabled by tailored ancillary ligand design", Nat. Commun., 2016, pp. 1-11, vol. 7.
Leadbeater, "When is free really free?", Nature Chemistry, 2010, pp. 1007-1009, vol. 2.
Li et al., "Detection of Trace Palladium in Flasks and Metal Reagents Using a Fluorogenic Tsuji-Trost Reaction", ChemPlusChem, 2012, pp. 281-283, vol. 77.
Li et al., "Design Strategies for Water-Soluable Small Molecular Chromogenic and Fluorogenic Probes", Chem Rev. 2014, pp. 590-659, vol. 114.
Li et al., "Colourimetric and fluorescent probes for the optical detection of palladium ions", Chem. Soc. Rev., 2013, pp. 7943-7962, vol. 42.
Liu et al., "Detection of trace levels of Pd2+ in pure water using a fluorescent probe assisted by surfactants", Sensors and Actuators B: Chemical, 2016, pp. 899-904, vol. 237.
Malatesta et al., "Platinum(0) Compounds with Triarylphosphines and Analogous Ligands", J. Chem Soc. 1958, pp. 2323-2328.
Messerschmidt et al., "The blue oxidases, ascorbate oxidase, laccase and ceruloplasmin Modelling and structural relationships", Eur. J. Biochem., 1990, pp. 341-352, vol. 187.
Mirnezami et al., "Preparing for Precision Medicine", N Engl J Med, 2012, pp. 489-491, vol. 366, No. 6.
Mjos et al., "Metallodrugs in Medicinal Inorganic Chemistry", Chem. Rev. 2014, pp. 4540-4563, vol. 114.
Montagner et al., "A Fluorescent Probe for Investigating the Activation of Anticancer Platinum(IV) Prodrugs Based on the Cisplatin Scaffold", Angew Chem., 2013, p. 12001-12005, vol. 125.
Niemeyer et al., "Parameterization of phosphine ligands reveals mechanistic pathways and predicts reaction outcomes". Nature Chemistry, 2016, pp. 610-617, vol. 8.
Ohshima et al., Platinum-Catalyzed Direct Amination of Allylic Alcohols under Mild Conditions: Ligand and Microwave Effects, Substrate Scope, and Mechanistic Study, J. Am. Chem. Soc., 2009, pp. 14317-14328, vol. 131.
Pershagen et al., "Designing reactivity-based responsive lanthanide probes for multicolor detection in biological systems", Coordination Chemistry Reviews, 2014, pp. 30-46, vol. 273-274.
Rae et al., "Undetectable Intracellular Free Copper: The Requirement of a Copper Chaperone for Superoxide Dismutase", Science, 1999, pp. 805-809, vol. 284.
Reed et al., "The measurement of cisplatin-DNA adduct levels in testicular cancer patients", Carcinogenesis, 1988, pp. 1909-1911, vol. 9, No. 10.
Ryan, "The Detection of Palladium, Platinum and Rhodium with p-Nitrosodiphenylamine", Analyst, 1951, pp. 167-171, vol. 76.
Sakurai et al., "Basic and Applied Features of Multicopper Oxidases, CueO, Bilirubin Oxidase, and Laccase", The Chemical Record, 2007, pp. 220-229, vol. 7.
Santra et al., "Fluorescent detection of palladium species with an O-propargylated fluorescein", Chem. Commun., 2010, pp. 3964-3966, vol. 46.
Schellens et al., "Relationship between the exposure to cisplatin, DNA-adduct formation in leucocytes and tumour response in patients with solid tumours", British Journal of Cancer, 1996, pp. 1569-1575, vol. 73.
Schuldes, et al., "Loss of In Vitro Cytotoxicity of Cisplatin after Storage as Stock Solution in Cell Culture Medium at Various Temperatures", Cancer, 1997, pp. 1723-1728, vol. 79.
Shan et al., "Coumarinic chaicone derivatives as chemosensors for cynaide anions and copper ions", Sensors and Actuators B: Chemical, 2015, pp. 463-469, vol. 221.
Shao et al."Enantioselective Copper-Catalyzed Propargylic Etherification of Propargylic Esters with Phenols Promoted by Inorganic Base Additives", Adv. Synth. Catal., 2016, pp. 2558-2563, vol. 358.
Shao et al., "Desilylation-Activated Propargylic Transformation: Enantioselective Copper-Catalyzed [3+2] Cycloaddition of Propargylic Esters with Beta-Naphthol or Phenol Derivatives", Angew. Chem. Int. Ed., 2016, pp. 5014-5018, vol. 55.
Shigehiro et al., "Novel 10,13-disubstituted dipyrido[3,2-alpha:2,3-c]phenazines and their platinum(II) complexes: highly luminescent

(56) References Cited

OTHER PUBLICATIONS

ICT-type fluorophores based on D—A—D structures", Tetrahedron Letters, 2014, pp. 5195-5198, vol. 55.
Simmons et al., "Catalytic functionalization of unactivated primary C—H bonds directed by an alcohol", Nature, 2012, pp. 70-73, vol. 483.
Singh et al., "Combinatorial approach to the development of fluorescent sensors for nanomolar aqueous copper", Tetrahedron Letters, 2000, pp. 9601-9605, vol. 41.
Song et al., "A Highly Sensitive Fluorescent Sensor for Palladium Based on the Allylic Oxidative Insertion Mechanism", J. Am., Chem. Soc., 2007, pp. 12354-12355, vol. 129.
Surry et al., "Dialkylbiaryl Phosphines in Pd-Catalyzed Amination: A User's Guide", Chem Sci., 2011, pp. 1-69, vol. 2, No. 1.
Sen et al. "Role of Transition Metal-Dioxygen Complexes in Catalytic Oxidation. Catalysis of the Oxidation of Phosphines by Dioxygen Adducts of Platinum", J. Am. Chem. Soc., 1977, pp. 8337-8339, vol. 99, No. 25.
Tainer et al., "Structure and mechanism of copper, zinc superoxide dismutase", Nature, 1983, pp. 284-287, vol. 306.
Tang et al., "Development of fluorescent probes based on protection-deprotection of the key functional groups for biological imaging", Chem Soc. Rev., 2015, pp. 5003-5015, vol. 44.
Thome et al., "Trace metal impurities in catalysis", Chem. Soc. Rev. 2012, pp. 979-987, vol. 41.
Trost et al., "Asymmetric Transition Metal-Catalyzed Allylic Alkylations", Chem., Rev., 1996, pp. 395-422, vol. 96.
Tsuchida et al., "Construction of Chiral Tri- and Tetra-Arylmethanes Bearing Quaternary Carbon Centers: Copper-Catalyzed Enantioselective Propargylation of Indoles with Propargylic Esters", Angew. Chem. Int. Ed., 2016, pp. 9728-9732, vol. 55.
Vandecasteele, et al., "Inductively Coupled Plasma Mass Spectrometry of Biological Samples", Journal of Analytical Atomic Spectrometry, 1993, pp. 781-786, vol. 8.
Wen et al., "A water-soluble near-infrared fluorescent probe for specific Pd2+ detection", Bioorganic & Medicinal Chemistry, 2018, pp. 931-937, vol. 26.
Williams et al., "A High-Throughput Method To Detect Palladium in Ores", Ind. Eng. Chem. Res., 2013, pp. 8612-8615, vol. 52.
Wu et al., "Catalytic Signal Amplification Using a Heck Reaction. An Example in the Fluorescence Sensing of Cu(II)", J. Am., Chem. Soc., 2004, pp. 14682-14683, vol. 126.
Xiao et al., "Copper regulates rest-activity cycles through the locus coeruleus-norepineprhine system", Nat Chem Biol. 2018, pp. 655-663, vol. 14:7.
Yang et al. "Imaging of the intracellular topography of copper with a fluorescent sensor and by synchrotron x-ray fluorescence microscopy", PNAS, 2005, pp. 11179-11184, vol. 102, No. 32.
Yang et al., "A new highly copper-selective fluorescence enhancement chemosensor based on BODIPY excitable with visible light and its imaging in living cells", Sensors and Actuators B: Chemical, 2016, pp. 110-117, vol. 224.
Yang et al., "A highly sensitive and selective fluorescent sensor for detection of copper ions based on natural Isorhamnetin from Ginkgo leaves", Sensors and Actuators B: Chemical, 2016, pp. 386-391, vol. 236.
Yun et al, "Diversity Oriented Fluorescence Library Approach (DOFLA) for Live Cell Imaging Probe Development", Acc. Chem. Res., 2014, pp. 1277-1286, vol. 47.
Zeng et al., "A Selective Turn-On Fluorescent Sensor for Imaging Copper in Living Cell", J Am Chem Soc., 2006, pp. 1-6, vol. 128:1.
Zhao et al. "A rhodamine-based chromogenic and fluorescent chemosensor for copper ion in aqueous media", Sensors and Actuators B: Chemical, 2009, pp. 625-631, vol. 135.
Zhou et al., "Cross-Coupling of Unactivated Secondary Alkyl Halides: Room-Temperature Nickel-Catalyzed Negishi Reactions of Alkyl Bromides and Iodides", J Am. Chem Soc., 2003, p. 14726-14727, vol. 125.
Zhou et al., "A novel ratiometric two-photon fluorescent probe for imaging of Pd2+ ions in living cells and tissues", Spectrochimica Acta Part A: Molecular and Biomolecular Spectroscopy, 2016, pp. 25-30, vol. 166.
Zhou et al., "A Turn-On Fluorescent Probe for Highly Selective and Sensitive Detection of Palladium", Chin. J. Chem., 2016, pp. 715-719, vol. 34.
Zimmermann et al., "Significance of Platinum Group Metals Emitted from Automobile Exhaust Gas Converters for the Biosphere", ESPR-Environ Sci & Pollut Res, 2004, pp. 194-199, vol. 11:3.

* cited by examiner

FLUORESCENT METHOD TO QUANTIFY COPPER OR PLATINUM BASED ON CATALYSIS

CROSS REFERENCE TO RELATED APPLICATIONS

This application claims the benefit of U.S. Provisional Patent Application No. 62/656,067, filed Apr. 11, 2018, which is incorporated herein by reference in its entirety.

STATEMENT OF FEDERAL FUNDING

This invention was made with government support under Grant No. CHE1506942 awarded by the National Science Foundation. The government has certain rights in the invention.

Provided herein are methods of identifying or quantifying copper or platinum in a test sample, and related kits and compositions.

With increasing demands for detecting and quantifying metals in nearly all areas of chemistry, pharmaceutical science, environmental science, and medicine, faster and less expensive methods are needed. In contrast to instrumental techniques for trace metal analysis, the use of chemosensors offers an inexpensive, fast, and on-site approach, and catalysis-based chemosensors can even rival instrumental techniques for sensitivity.

A fluorescence sensor capable of detecting and quantifying copper in both aqueous samples and intracellularly is highly desirable. Because copper is also a widely-used metal in organic synthesis, these sensors would be valuable for use in determining copper concentrations after copper-catalyzed reactions, such as in the pharmaceutical industry. Most chemosensors for copper rely on the coordination of $Cu^+$ or $Cu^{2+}$ to either turn off or turn on fluorescence. Current copper chemosensors have several limitations, such as poor selectivity over other metals, high detection limits, and the requirement of many synthetic steps. Additionally, some of these sensors cannot be used in cellular imaging.

Quantification of heavy metals continues to rely on instrument-intensive techniques such as inductively-coupled plasma mass spectroscopy (ICP-MS). Although a few sensors exist for platinum, truly selective fluorometric methods for platinum ions have not yet been developed—especially with selectivity over palladium. The contamination of palladium in commercial reagents, including phosphines, is well known. Additionally, platinum and palladium co-exist in geological and automobile emission samples, necessitating platinum-selective methods in mining operations and environmental monitoring. Therefore, it is desirable to minimize interference by palladium in platinum detection methods. Moreover, platinum drugs are the most widely used cancer chemotherapeutics, representing another application where the development of a platinum sensor would be valuable.

Methods to detect copper and platinum that are highly selective, rapid, and broadly available are therefore desirable.

SUMMARY

In one aspect of the invention, a method of identifying or quantifying copper in a test sample is provided. The method comprises mixing, thereby producing a reaction mixture: the test sample; a triaryl phosphine represented by Formula 1a, optionally dissolved in a solvent,

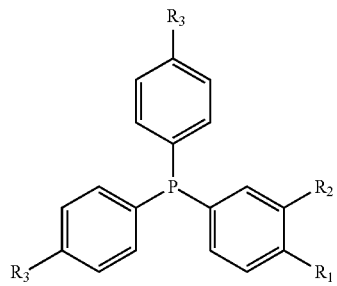

Formula 1a wherein $R_1$ is hydrogen, dialkylamino, $C_{1-6}$ alkyl, fluoro, or $C_{1-6}$ alkoxy; $R_2$ is hydrogen or $SO_3^-$; and $R_3$ is hydrogen, $C_{1-6}$ alkyl, fluoro, amino, or $C_{1-6}$ alkoxy; and a propargyl fluorochrome ether or carbamate, that, when subjected to a depropargylation reaction, results in an increase in fluorescence of the depropargylated fluorochrome as compared to the propargyl fluorochrome at a suitable excitation wavelength of at least 10 times; and reacting the test sample, the triaryl phosphine, and the propargyl fluorochrome ether or carbamate for a time, temperature, and pH sufficient to cause the depropargylation of the propargyl fluorochrome ether or carbamate in the presence of copper in the sample.

In another aspect, a method of identifying or quantifying platinum in a test sample is provided. The method comprises mixing, thereby producing a reaction mixture: the test sample; a triaryl phosphine represented by Formula 1b,

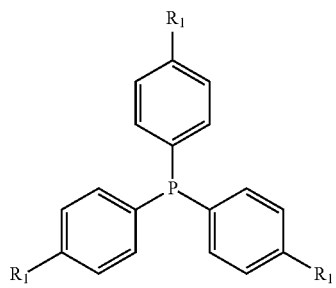

Formula 1b wherein $R_1$ is fluoro, $C_{1-6}$ alkoxy, $C_{1-6}$ alkyl, or hydrogen; or Formula 1c,

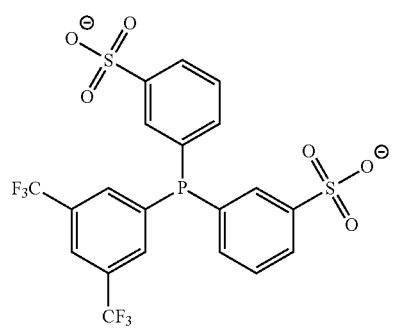

Formula 1c optionally dissolved in a solvent; and an allyl fluorochrome ether or carbamate, that, when subjected to a deallylation reaction, results in an increase in fluorescence of the deallylated fluorochrome ether or carbamate as compared to the allyl fluorochrome ether or carbamate at a suitable excitation wavelength of at least 10 times; and reacting the test sample, the triaryl phosphine, and the allyl fluorochrome ether or carbamate for a time, temperature, and pH sufficient to cause the allylation of the allyl fluorochrome ether or carbamate in the presence of platinum in the sample.

In another aspect, a kit is provided for use in identifying or quantifying platinum in a test sample. The kit comprising in one or more vessels or containers, a triaryl phosphine represented by Formula 1b,

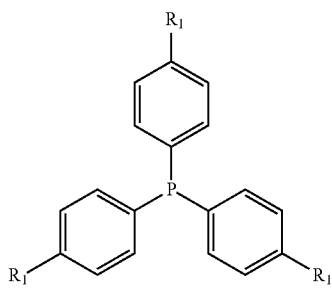

Formula 1b wherein $R_1$ is fluoro, alkoxy, alkyl, or hydrogen; or Formula 1c,

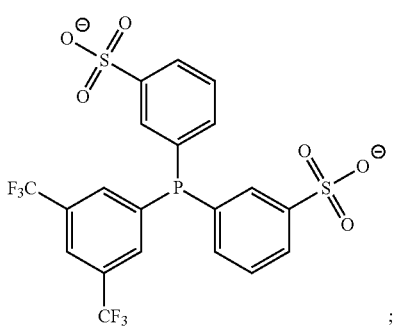

Formula 1c an allyl fluorochrome ether or carbamate, such as allyl Pittsburgh Green ether (APE), and, optionally, a reducing agent, such as sodium borohydride.

In yet another aspect, a kit is provided for use in identifying or quantifying copper in a test sample comprising in one or more vessels or containers, a triaryl phosphine represented by Formula 1a,

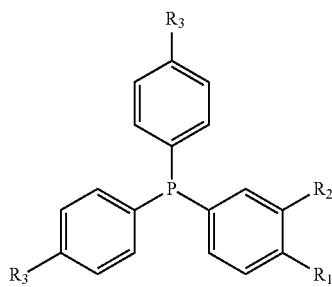

Formula 1a wherein $R_1$ is hydrogen, dialkylamino, or alkoxy; $R_2$ is hydrogen or $SO_3$; and $R_3$ is hydrogen or alkoxy; a propargyl fluorochrome ether or carbamate, such as propargyl Pittsburgh Green ether (PPE), and, optionally, a reducing agent.

BRIEF DESCRIPTION OF THE DRAWINGS

FIG. 1B: Ligands tested for the depropargylation of PPE and the deallylation of APE with various metals.

DETAILED DESCRIPTION

Figure 1A:
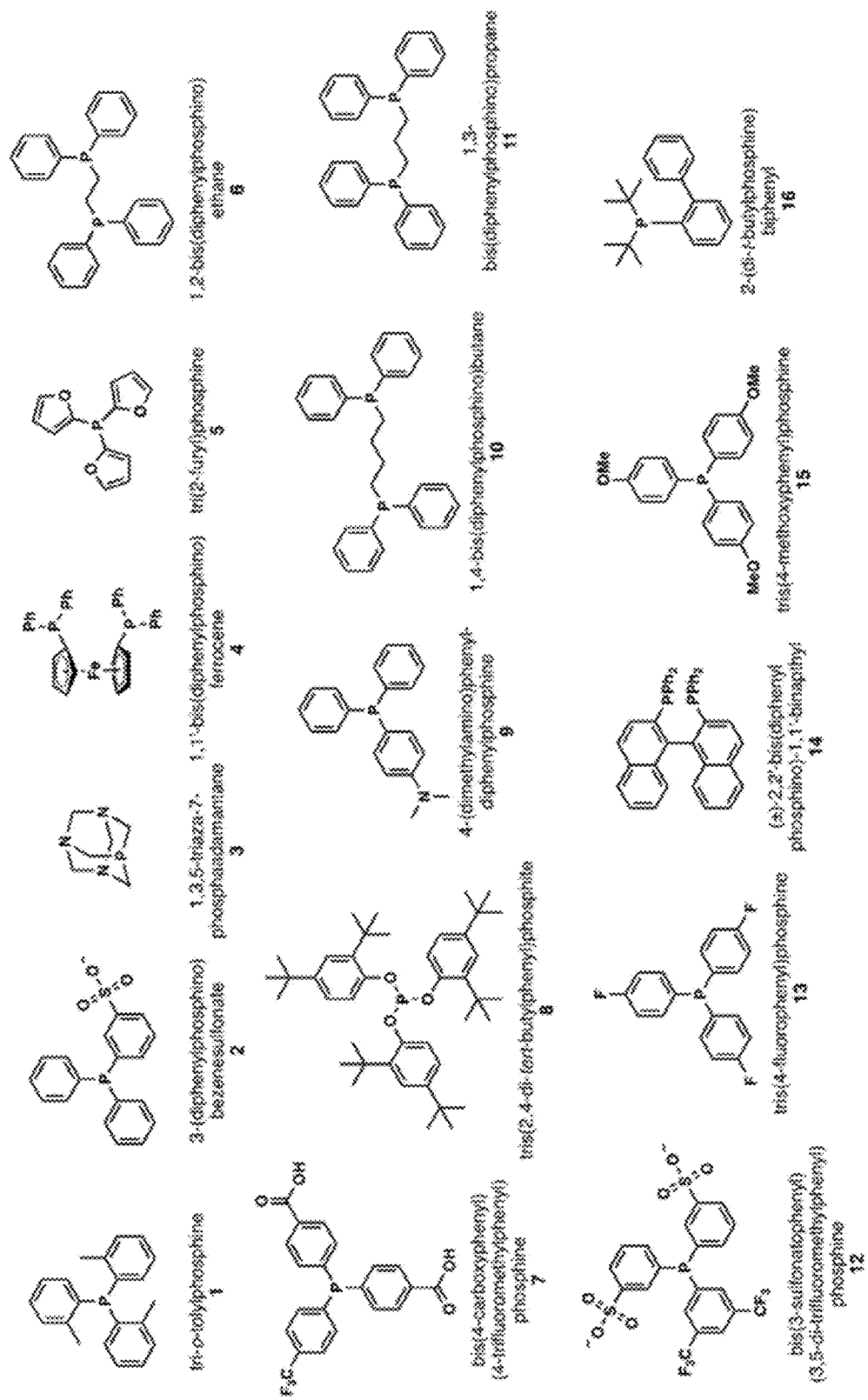
FIG. 1A: Ligands tested for the depropargylation of PPE and the deallylation of APE with various metals.

Other than in the operating examples, or where otherwise indicated, the use of numerical values in the various ranges specified in this application are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. Further, as used herein, all numbers expressing dimensions, physical characteristics, processing parameters, quantities of ingredients, reaction conditions, and the like, used in the specification and claims are to be understood as being modified in all instances by the term "about". Moreover, unless otherwise specified, all ranges disclosed herein are to be understood to encompass the beginning and ending range values and any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 3.3, 4.7 to 7.5, 5.5 to 10, and the like.

As used herein "a" and "an" refer to one or more. The term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention.

As used herein, the term "aryl" refers to a monocyclic or polycyclic aromatic hydrocarbon radical. As used herein, the term "aromatic" refers to a cyclically conjugated molecular entity with a stability (due to delocalization) significantly greater than that of a hypothetical localized structure. An example of an aryl group is phenyl, optionally substituted by, for example, halogen, alkyl, alkoxy, sulfonate, or amino groups. As used herein, the term "triaryl" refers to three aryl groups.

As used herein, the term "alkyl" refers to monovalent groups derived from alkanes by removal of a hydrogen atom from any carbon atom. Alkyl groups include linear or branched, cyclic or acyclic hydrocarbon groups. Example of alkyl groups include methyl, ethyl, propyl, isopropyl, butyl, sec-butyl, tert-butyl, pentyl, neopentyl, and cyclohexyl. The term "$C_1$-$C_6$ alkyl" refers to an alkyl group having a total of 1 to 6 carbon atoms.

A "substituent", as used herein, refers to an atom or group of atoms which replaces one or more hydrogen atoms on the parent chain of a molecule.

As used herein, the term "alkoxy" refers to an alkyl group singularly bonded to oxygen (—OR, wherein R is alkyl). Examples of alkyl groups include methoxy, ethoxy, propoxy, isopropoxy, butoxy, tert-butoxy, and neopentoxy. The term "$C_1$-$C_6$" alkoxy refers to an alkoxy group having a total of 1 to 6 carbon atoms.

As used herein, the term "amino" refers to a nitrogen atom attached by single bonds to hydrogen atoms, alkyl groups, aryl groups, or a combination thereof. For example, the amino group may be a dialkylamino group, —$NR_2$, wherein R is an alkyl group. The alkyl groups of the dialkylamino group may be the same or different. Examples of dialkylamino groups include dimethylamino and diethylamino.

As used herein, the term "propargyl" refers to an alkyl functional group of 2-propynyl (HC≡C—$CH_2$—). As used herein, the term "depropargylation" refers to a reaction which removes a propargyl group from a molecule, wherein a covalent bond between the molecule and the propargyl group is broken. As used herein, the term "allyl" refers to an alkyl functional group with the structural formula $H_2$C═CH—$CH_2$—. As used herein, the term "deallylation" refers to a reaction which removes an allyl group from a molecule, wherein a covalent bond between the molecule and the allyl group is broken.

As used herein, the term "fluorochrome" refers to a compound that fluoresces. A "propargyl fluorochrome" refers to a fluorochrome having a propargyl group. The propargyl fluorochrome may be a latent fluorochrome that becomes fluorescent upon removal of the propargyl group. An "allyl fluorochrome" refers to a fluorochrome having an allyl group. The allyl fluorochrome may be a latent fluorochrome that becomes fluorescent upon removal of the allyl group.

As used herein, the term "ether" refers to an organic compound that comprises an oxygen atom connected to two alkyl or aryl groups. As used herein, the term "propargyl ether" refers to a compound comprising the functional group

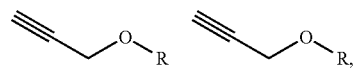

wherein R is an alkyl or an aryl group. As used herein, the term "allyl ether" refers to a compound comprising the functional group

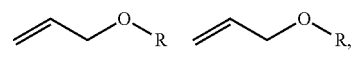

wherein R is an alkyl or an aryl group.

As used herein, the term "carbamate" refers to an organic compound comprising the group $R_2NCOOR'$, wherein R is a hydrogen, alkyl, or aryl group and R' is an alkyl or aryl group. As used herein, the term "propargyl carbamate" refers to a compound comprising the functional group $R_2NCOOR'$ wherein R' is a propargyl group. As used herein, the term "allyl carbamate" refers to a compound comprising the functional group $R_2NCOOR'$ wherein R' is an allyl group.

As used herein, the unit "μM" refers to micromolar, "mM" refers to millimolar, "M" refers to molar, "A.U." to arbitrary units, and "nm" to nanometers.

A method of identifying or quantifying copper in a test sample is provided. The method comprises mixing, thereby producing a reaction mixture comprising: the test sample, a phosphine, and a propargyl fluorochrome. The test sample may comprise copper, such as $Cu^+$ and/or $Cu^{2+}$.

The phosphine utilized in the method for identifying or quantifying copper may be a triaryl phosphine. The phosphine may act as a ligand and bind to copper to form a copper-phosphine complex. In embodiments, the triaryl phosphine for use in the method for identifying or detecting copper may be represented by Formula 1a:

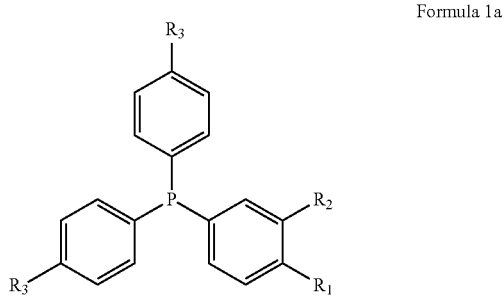

Formula 1a

With reference to Formula 1a, $R_1$ is hydrogen, amino, alkyl, fluoro, or alkoxy, $R_2$ is hydrogen or $SO_3^-$, and $R_3$ is hydrogen, alkyl, fluoro, amino, or alkoxy. Examples of groups from which $R_1$ can be selected include alkylamino, dialkylamino, $C_{1-6}$ alkyl, and $C_{1-6}$ alkoxy. For example, $R_1$ can be dimethylamino, methyl, or methoxy. Examples of groups from which $R_3$ can be selected include $C_{1-6}$ alkyl and $C_{1-6}$ alkoxy. For example, $R_3$ can be methyl or methoxy. The triarylphosphine may be selected to have at least one para-substituent or at least one ortho-substituent.

Figure 1B:
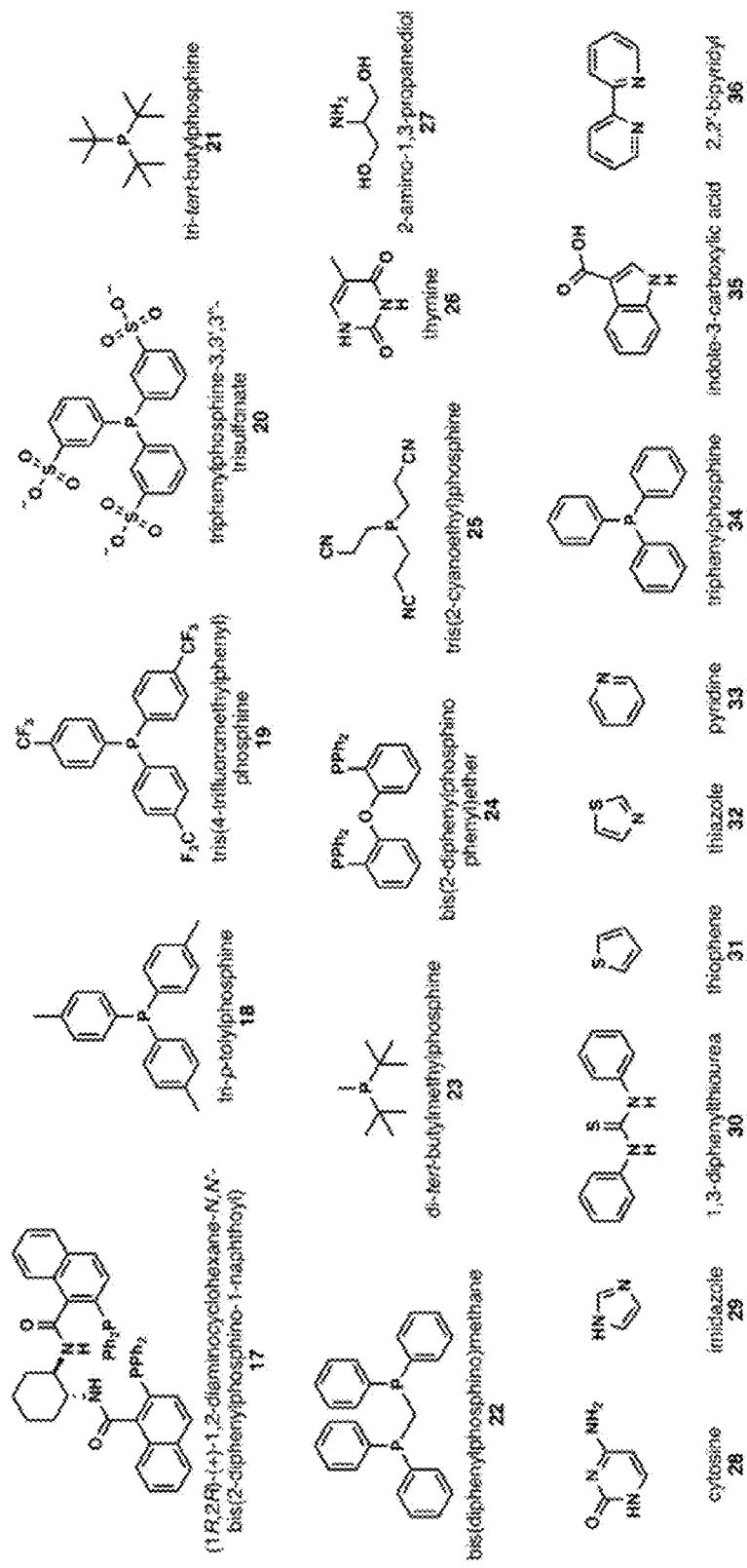
FIG. 1B.

Examples of suitable triaryl phosphines for use in the copper detection method of the present disclosure include 3-(diphenylphosphino)benzenesulfonate, 4-(dimethylamino)phenyldiphenylphosphine, tris(4-methoxyphenyl)phosphine, tri-p-tolylphosphine, and triphenylphosphine (compounds 2, 9, 15, 18 and 34, respectively, in FIGS. 1A and 1B).

The phosphine may be dissolved in a solvent, such as a polar solvent. The solvent may be a polar aprotic solvent such as acetonitrile, dimethylsulfoxide, or N-methylpyrrolidone. The solvent may be a polar protic solvent, such as an alcohol solvent, for example, ethanol. The solvent may be present in an amount of from 1 to 70%, such as from 5 to 25%, such as 15%. The solvent may be present in amount of no greater than 50%, or no greater than 25%. The phosphine may be present in the reaction mixture at a concentration of from 1 μM to 1000 μM, from 1 μM to 500 μM, from 1 μM to 200 μM, or from 100 μM to 200 μM, such as 160 μM, depending on the solubility of the specific phosphine. The phosphine may be present in the reaction mixture at a concentration of at least 50 μM or at least 100 μM.

Figure 2:
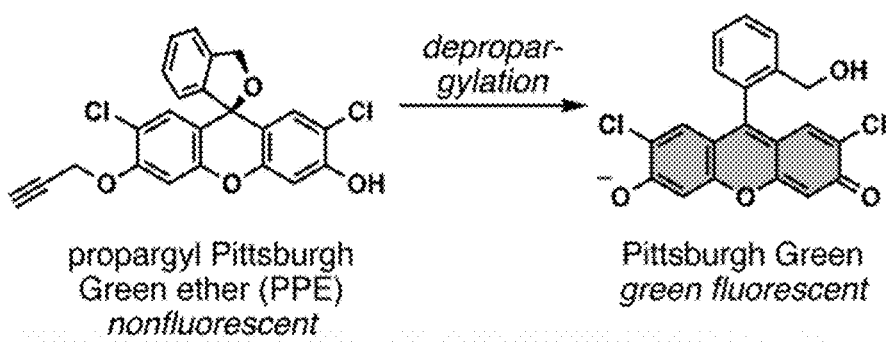
FIG. 2: Depropargylation of PPE to produce a fluorescent molecule, Pittsburgh Green.

The propargyl fluorochrome may be a propargyl fluorochrome ether, such as propargyl Pittsburgh green ether (PPE). The propargyl fluorochrome may be a propargyl fluorochrome carbamate. The propargyl fluorochrome is subjected to a depropargylation reaction, wherein the propargyl group is removed. An example of a depropargylation reaction of PPE is shown in FIG. 2. The propargyl fluorochrome is selected such that, when subjected to a depropargylation reaction, an increase in fluorescence of the depropargylated fluorochrome as compared to the propargyl fluorchrome results. The increase in fluorescence of the depropargylated fluorochrome as compared to the propargyl fluorochrome, at a suitable excitation wavelength, may be at least 10 times greater, at least 20 times greater, at least 25 times greater, at least 50 times greater, at least 100 times greater, at least 200 times greater, at least 300 times greater, or at least 400 times greater. For example, the fluorescence intensities for the Pittsburgh Green fluorophore and PPE are vastly different (200-400:1), providing a sensitive platform for metal detection. The excitation wavelength (hex) for the propargyl fluorochrome may be in the range of from 400 nm to 525 nm, such as between 400 nm and 600 nm, or between 450 nm and 500 nm. The emission wavelength (Aem) for the propargyl fluorochrome ranges from 500 nm to 550 nm, such as from 400 nm to 600 nm, or from 510 nm to 570 nm.

The method of identifying or quantifying copper of the present disclosure includes reacting the test sample, the phosphine, and the propargyl fluorochrome for a time, temperature, and pH sufficient to cause the depropargylation of the propargyl fluorochrome in the presence of copper in the sample. For example, the reaction may be performed for a time in the range of 1 minute to 24 hours, as long as the reaction solution is covered to prevent evaporation, such as from 10 minutes to 3 hours, such as from 20 minutes to 2 hours. The reaction may be performed at a temperature of from 20° C. to 45° C., such as from 24° C. to 31° C., from 20° C. to 25° C., such as room temperature (25° C.). The reaction may be performed at a pH of at least 7 or at least 8. The reaction may be performed at a pH in the range of from 7 to 11, from 7 to 10, from 7 to 9, from 8 to 10, or from 8 to 9.

The reaction mixture may include a buffer salt. The buffer salt may be, for example, phosphate, bicarbonate, borate, or carbonate. The buffer may be present in the reaction mixture at a concentration in the range of 10 mM to 1.5 M, from 15 mM to 1.2 M, or from 15 mM to 100 mM, such as 50 mM.

The depropargylation reaction of the propargyl fluorochrome in the presence of copper and the phosphine may be a catalytic reaction. That is, the copper in the test sample, in the presence of phosphine, may act as a catalyst for the depropargylation of the propargyl fluorochrome.

The method of identifying copper of the present disclosure may be able to detect copper in test samples with copper concentrations as low as 20 μM, 10 μM, 1 μM, 100 nM, 10 nM, 5 nM, or 4.5 nM. The method of quantifying copper of the present disclosure may be able to quantify copper in test samples with copper concentrations as low as 20 μM, 10 μM, 1 μM, 100 nM, 50 nM, 20n M, or 15 nM. The method of identifying or quantifying copper of the present disclosure may be able to detect or quantify copper in test samples with copper concentrations as low as 300 ppm, 100 ppm, or 30 ppm.

The method of identifying or quantifying copper of the present disclosure may be selective for the detection of $Cu^+$ and/or $Cu^{2+}$ ions over other metal ions. For example, the method may be more selective for the detection of copper over the detection of silver, gold, cadmium, cerium, cobalt, chromium, iron, mercury, magnesium, manganese, nickel, lead, rhodium, ruthenium, strontium, zinc, palladium, and/or platinum. For example, the method of detection may be $10^4$, $10^5$, or $10^6$ times more selective for copper than for other metals.

A method of identifying or quantifying platinum in a test sample is provided. The method comprises mixing, thereby producing a reaction mixture comprising: the test sample, a phosphine, and an allyl fluorochrome. The test sample may comprise platinum, such as $Pt^{2+}$.

The phosphine utilized in the method for identifying or quantifying platinum may be a triaryl phosphine. The phosphine may act as a ligand and bind to platinum to form a platinum-phosphine complex. In embodiments, the triaryl phosphine for use with the method for identifying or quantifying platinum may be represented by Formula 1b:

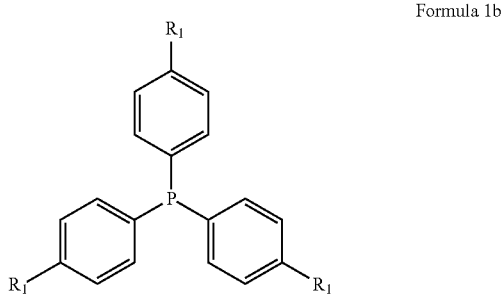

Formula 1b

With reference to Formula 1b, $R_1$ is hydrogen, fluoro, or alkyl. Examples of alkyl groups from which $R_1$ can be selected include $C_{1-6}$ alkyl, such as methyl. Examples of methoxy groups from which $R_1$ can be selected include $C_{1-6}$ alkoxy, such as methoxy.

Alternatively, the triaryl phosphine for use with the method for identifying or quantifying platinum may be represented by Formula 1c:

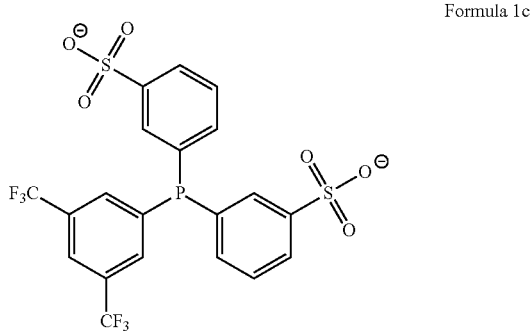 [SMILES: O=S(=O)([O-])c1cccc(P(c2cc(C(F)(F)F)cc(C(F)(F)F)c2)c2cccc(S(=O)(=O)[O-])c2)c1]

Formula 1c

Examples of suitable triaryl phosphines for use in the platinum detection method of the present disclosure include bis(3-sulfonatophenyl)(3,5-di-trifluoromethylphenyl)phosphine (as shown in Formula 1c), tris(4-fluorophenyl)phosphine, tris(4-methoxyphenyl)phosphine, tri-p-tolylphosphine, and triphenylphosphine (compounds 12, 13, 15, 18, and 34, respectively, in FIGS. 1A and 1B).

The phosphine may be dissolved in a solvent, such as a polar solvent. The solvent may be a polar aprotic solvent such as acetonitrile, dimethylsulfoxide, or N-methylpyrrolidone. The solvent may be a polar protic solvent, such as an alcohol solvent, for example, ethanol. The solvent may be present in an amount of from 1 to 70%, such as from 5 to 25%, such as 10%. The solvent may be present in amount of no greater than 50%, or no greater than 25%. The phosphine may be present in the reaction mixture at a concentration of from 1 µM to 500 µM, from 10 µM to 200 µM, or from 100 µM to 200 µM, such as 200 µM. The phosphine may be present in the reaction mixture at a concentration of at least 50 µM or at least 100 µM.

The allyl fluorochrome may be an allyl fluorochrome ether or carbamate. The allyl fluorochrome may be an allyl fluorochrome ether, such as allyl Pittsburgh green ether (APE).

Figure 3:
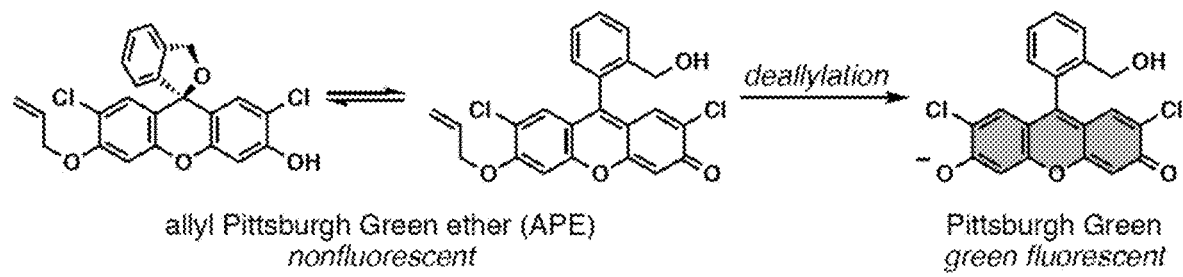
FIG. 3: Deallylation of APE to produce a fluorescent molecule, Pittsburgh Green.

The allyl fluorochrome is subjected to a deallylation reaction, wherein the allyl group is removed. An example of a deallylation reaction of APE is shown in FIG. 3. The allyl fluorochrome is selected such that, when subjected to an allylation reaction, an increase in fluorescence of the deallylated fluorochrome as compared to the allyl fluorchrome results. The increase in fluorescence of the deallylated fluorochrome as compared to the allyl fluorochrome, at a suitable excitation wavelength, may be at least 10 times greater, at least 20 times greater, at least 25 times greater, at least 50 times greater, at least 100 times greater, at least 200 times greater, at least 300 times greater, or at least 400 times greater. The excitation wavelength (λex) for the propargyl fluorochrome may be in the range of from 400 nm to 525 nm, such as between 400 nm and 600 nm, or between 450 nm and 500 nm. The emission wavelength (λem) for the propargyl fluorochrome ranges from 500 nm to 550 nm, such as from 400 nm to 600 nm, or from 510 nm to 570 nm.

The method of identifying or quantifying platinum of the present disclosure includes reacting the test sample, the phosphine, and the allyl fluorochrome for a time, temperature, and pH sufficient to cause the deallylation of the allyl fluorochrome in the presence of platinum in the sample. For example, the reaction may be performed for a time in the range of 1 minute to 24 hours, as long as the reaction solution is covered to prevent evaporation, such as from 10 minutes to 3 hours, such as from 20 minutes to 2 hours. The reaction may be performed at a temperature of from 20 to 50° C., from 20 to 35° C., from 24° C. to 31° C., or from 20 to 25° C., such as room temperature. The reaction may be performed at a pH of at least 7 or at least 8. The reaction may be performed at a pH in the range of from 7 to 11, from 7 to 10, from 7 to 9, from 8 to 10, or from 7 to 8.

The reaction mixture may include a buffer salt. The buffer salt may be, for example, phosphate, bicarbonate, borate, or carbonate. The buffer may be present in the reaction mixture at a concentration in the range of 10 mM to 1.5 µM, from 15 mM to 1.2 µM, or from 15 mM to 100 mM, such as 50 mM.

The deallylation reaction of the allyl fluorochrome in the presence of the test sample comprising platinum and the phosphine may be a catalytic reaction. That is, the platinum in the test sample, in the presence of phosphine, may act as a catalyst for the deallylation of the allyl fluorochrome.

The method of identifying platinum of the present disclosure may be able to detect platinum in test samples with platinum concentrations as low as 20 µM, 10 µM, 1 µM, 100 nM, 10 nM, 6 nM, or 5.5 nM. The method of quantifying platinum of the present disclosure may be able to quantify platinum in test samples with platinum concentrations as low as 20 µM, 10 µM, 1 µM, 100 nM, 50 nM, 20 nM, or 18 nM.

The method of identifying or quantifying platinum of the present disclosure may be selective for the detection of Pt(IV), Pt(II), and Pt(0) over other metal ions. For example, the method of identifying or quantifying platinum may be more selective for the detection of platinum over the detection of silver, gold, cadmium, cerium, cobalt, chromium, copper, iron, mercury, magnesium, manganese, nickel, rhodium, strontium, zinc, and/or palladium. For example, the method of detection may be 5, 10, 50 or 100 times more selective for platinum than for other metals.

The test sample to be used with the methods of the present invention may be an aqueous or biological sample. For example, the sample may be drinking water, proteins, live or fixed cells (e.g., in situ), or a biological fluid, such as blood, serum, plasma, urine, saliva, or cerebrospinal fluid. The test sample may be a solid state sample. The test sample may comprise an organic compound and/or an inorganic compound. The test sample may be or comprise a pharmaceutical sample, such as a drug compound. Examples of platinum-containing drug compounds include cisplatin, carboplatin, and oxaliplatin. The test sample may be a geological samples, such as a rock or rock extract.

The method for identifying or quantifying copper or the method for identifying or quantifying platinum may further comprise incubating the test sample with a chloride salt, such as lithium chloride or sodium chloride, or other salts providing a strongly electronegative ion, e.g., hard ligands, before adding the fluorochrome and the phosphine. This may be useful for the detection of copper or platinum in samples that are strongly ligated, such as carboplatin. The chloride ion may displace ligands from the platinum or copper in the sample.

The method for identifying or quantifying copper or the method for identifying or quantifying platinum may further comprise adding a reducing agent to the reaction mixture and thereby reacting the reducing agent with the test sample, the triaryl phosphine, and the fluorochrome. The reducing agent may be an alkali metal compound, such as sodium borohydride ($NaBH_4$), or other reducing agents that can reduce Pt(IV) to Pt(II) or Pt(II) to Pt(0). This may be useful for the detection of copper or platinum in samples that are strongly ligated or very stable, such as carboplatin or oxaliplatin. The reducing agent may reduce the copper or the platinum in the sample and/or result in the dissociation of ligands from copper or platinum in the test sample. For example, the reducing agent may reduce the platinum in the test sample to Pt(O).

A kit for use in identifying or quantifying platinum in a test sample also is provided. The kit comprises in one or more vessels, a triaryl phosphine represented by Formula 1b or Formula 1c, as described above, and an allyl fluorochrome ether or carbamate. The allyl fluorochrome ether or carbamate may be APE. The kit may include a reducing agent, such as $NaBH_4$.

A kit for use in identifying or quantifying copper in a test sample is also provided. The kit comprises, in one or more vessels, a triaryl phosphine represented by Formula 1a, as described above, and a propargyl fluorochrome ether or carbamate. The propargyl fluorochrome ether or carbamate may be PPE. The kit may include a reducing agent, such as $NaBH_4$.

A kit may further comprise one or more additional reagents, solvents, buffer solutions, and/or control reagents, such as Pittsburgh Green for instrument calibration. Also, the kit may comprise a suitable container or other packaging for containing, shipping, distributing, and/or storing the various components of the kit.

The assays described herein may be wholly or partially automated. The methods described herein may be adapted to and performed by a suitable off-the-shelf, or custom manufactured device comprising suitable mechanical, electronic, robotic, fluidic, and optical systems for performing all or part of the described methods. As such, a kit includes one or more cartridges conformed or adapted for use in an automated or semiautomated system. In one aspect, individual cartridges, with each containing a different reagent, are provided in a kit or separately, e.g., with a described phosphine ligand provided in a first cartridge, and the described propargyl or allyl fluorochrome in a second cartridge. In another aspect, a single cartridge is provided having a described phosphine ligand and a described propargyl or allyl fluorochrome provided together in a single compartment in the cartridge, or separately, in separate compartments of the cartridge. The reagents present in the cartridge may be dry or solubilized in a suitable solvent. The cartridge may be a single-use cartridge or a multiple-use cartridge. Choice and configuration of suitable cartridge designs, reagents to be contained in the cartridge, and the physical state of reagents in the cartridge is a matter of optimization for any platform using the cartridge.

Figure 4:
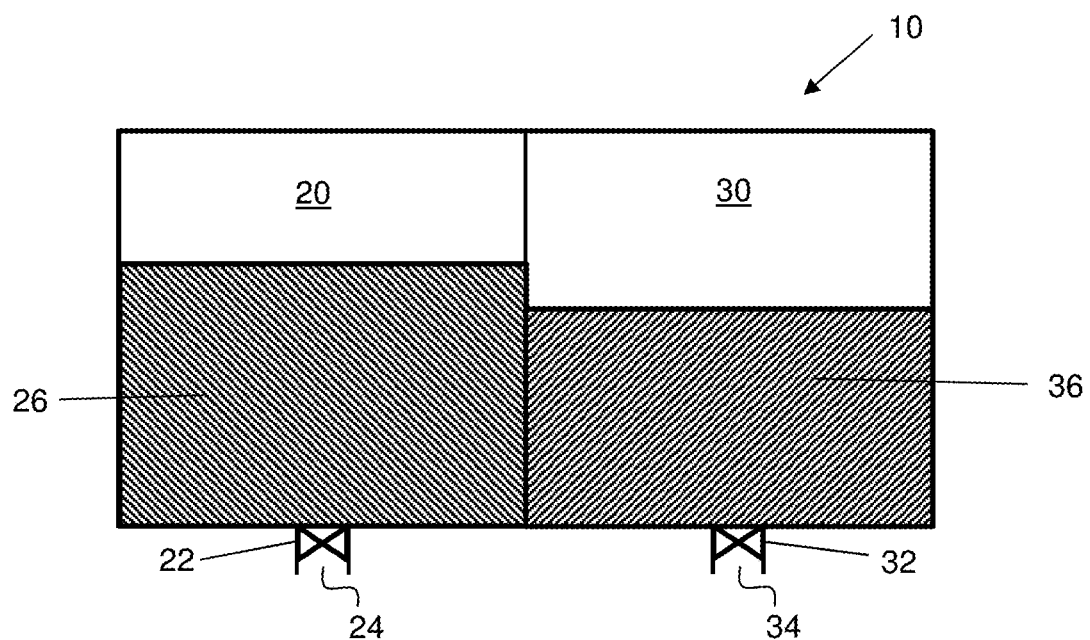
FIG. 4 provides a schematic diagram of a cross section of a cartridge.

FIG. 4 depicts schematically a cartridge 10. Cartridge 10 comprises a first chamber 20 having an outlet 22 with a valve 24, and a first solution comprising a first reagent 26, such as the described phosphine ligand. In use, valve 24 is opened to permit removal or discharge of the first reagent 26 from the first chamber 20. A second chamber 30 is depicted, comprising an outlet 32, a valve 34, and a second solution comprising a second reagent 36, such as the allyl or propargyl fluorochrome as described. Valves 24, 34 may be operated together or independently.

EXAMPLES

Fluorescence Measurements

All fluorescence measurements were obtained using a Modulus II Microplate Multimode Reader. Fluorescence was measured after exciting samples with 490 nm light and emission was measured between 510-570 nm. All fluorescence measurements were obtained at room temperature.

The Depropargylation of Fluorochrome with Various Metals and Ligands

Metals and ligands were combinatorially screened in the presence of Propargyl Pittsburgh Green ether (PPE) to determine which metals and ligands facilitated the depropargylation reaction.

Solid $AgNO_3$ and $Sr(NO_3)_2$ were dissolved in 5% $HNO_3$ (TraceMetal Grade) to a final concentration of 10 mM. $AuCl_3$, $CdCl_2$, $CeCl_3$, $CoCl_2$, $CuCl$, $CuCl_2$, $CrCl_2$, $Na_2Cr_2O_7$, $FeSO_4$, $FeCl_3$, $HgCl_2$, $MgCl_2$, $KMnO_4NiCl_2$, $Pb(OAc)_4$, $Rh(OAc)_2$, $RhCl_3$, $RuCl_3$, and $ZnCl_2$ were dissolved in 3% HCl (TraceMetal Grade) to a final concentration of 10 mM. Wilkinson's catalyst, as a source of Rh(I), was dissolved in DMSO to a final concentration of 5 mM. $RuCl_2$ (p-cymene) dimer was dissolved in DMSO to a final concentration of 5 mM (10 mM with respect to the monomer). Standard solutions of 1000 ppm $Pt^{2+}$ in 3% HCl and 1000 ppm $Pd^{2+}$ in 5% $HNO_3$ were used.

The ligands tested are shown in FIGS. 1A and 1B. Tri-o-tolylphosphine (1), 3-(diphenylphosphino)bezenesulfonic acid sodium salt (2), 1,3,5-triaza-7-phosphaadamantane (3), 1,1'-bis(diphenylphosphino)ferrocene (4), tri (2-furyl)phosphine 5), 1,2-bis(diphenylphosphino)ethane (6), bis(4-carboxyphenyl)(4-trifluoromethylphenyl)phosphine (7), tris(2,4-di-tert-butylphenyl)phosphite (8), 4-(dimethylamino)phenyl-diphenylphosphine (9), 1,4-bis(diphenylphosphino)butane (10), 1,3-bis(diphenylphosphino)

propane (11), bis(3-sulfonatophenyl)(3,5-ditrifluoromethylphenyl)phosphine disodium salt (12), tris(4-fluorophenyl)phosphine (13), (+)-2,2'-bis(diphenylphosphino)-1,1'-binapthyl (14), tris(4-methoxyphenyl)phosphine (15), 2-(di-t-butylphosphine)biphenyl (16), (1R,2R)-(+)-1,2-diaminocyclohexane-N—N'-bis(2-diphenylphosphino-1-naphthoyl) (17), tri-p-tolylphosphine (18), tris(4-trifluoromethylphenyl)phosphine (19), triphenylphosphine-3,3',3''-trisulfonic acid trisodium salt (20), tri-tert-butylphosphonium tetrafluoroborate (21), bis(diphenylphosphino)methane (22), di-t-butylmethylphosphonium tetrafluoroborate (23), bis(2-diphenylphosphinophenyl)ether (24), tris(2-cyanoethyl)phosphine (25), thymine (26), 2-amino-1,3-propanediol (27), cytosine (28), imidazole (29), 1,3-diphenylthiourea (30), thiophene (31), thiazole (32), pyridine (33), triphenylphosphine (34), indole-3-carboxylic acid (35), 2,2'-bipyridyl (36) were dissolved in DMSO to a final concentration of 20 mM.

A mixture containing 1.2 M pH 7.0 phosphate buffer (177.2 mL), DMSO (19.42 mL), and 8.0 mM PPE (556 µL) was separated into 37 aliquots. To these aliquots one of each of the 20 mM ligands (55.5 µL) was added; to one aliquot, no ligand was added. These solutions containing the probe and ligand (180 µL), termed working solutions, were transferred to a black 96-well plate. The metal solutions were diluted to 10 M using ultrapure water as the diluent. The 10 µM metal solutions (20 µL), as well as a no metal control sample, were then transferred to the wells containing the working solutions and the fluorescence was measured.

Figure 5:
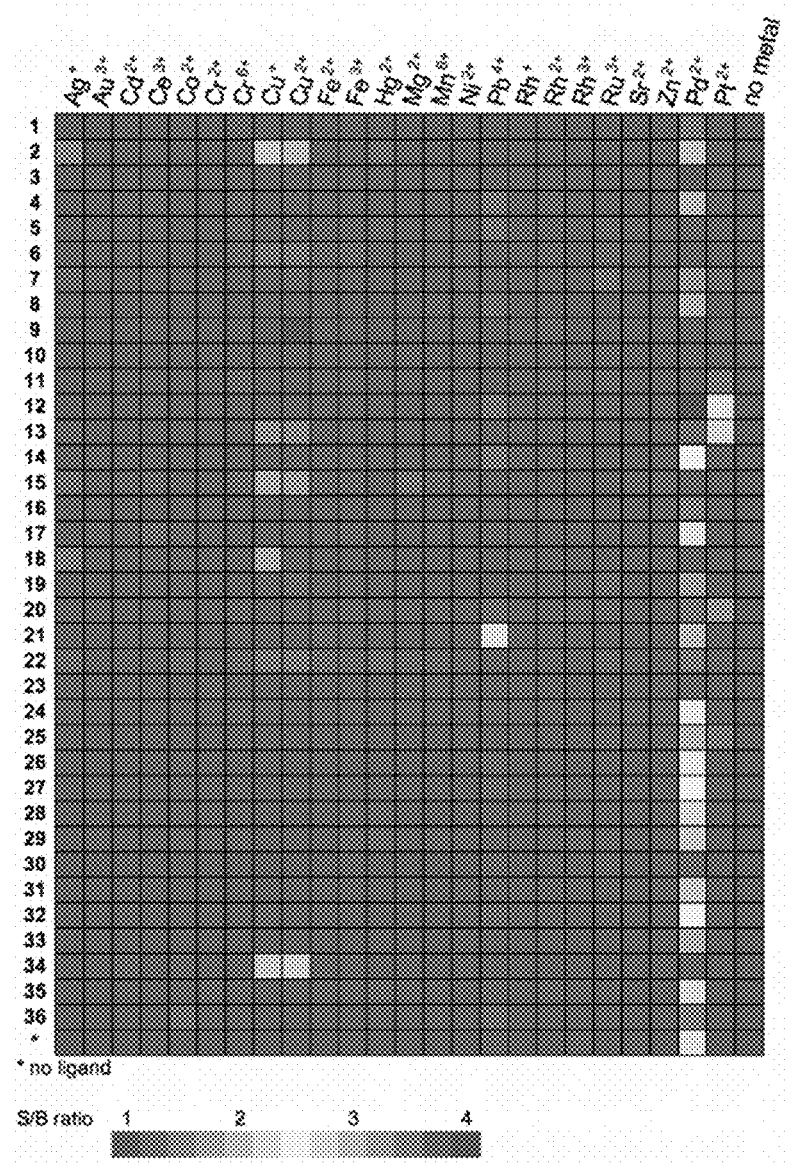
FIG. 5: Heat map of ligand vs. metal screen using PPE with ligand. Row 37 contains no ligand.

To analyze the data, each working solution was normalized, with the no metal sample normalized to 1. FIG. 5 shows a heat map with signal-to-background (S/B) ratios of fluorescence intensity.

We discovered that $Cu^+$ and $Cu^{2+}$ in the presence of electron-rich phosphine 9, 4-(dimethylamino)phenyldiphenylphosphine (hereafter referred to as DMAPPP), greatly increased the fluorescence signals. $Cu^+$ and $Cu^{2+}$ in the presence of 18 (tri-p-tolylphosphine), 15 (tris(4-methoxyphenyl)phosphine, 2 (3-(diphenylphosphino)benzenesulfonate), and 34 (triphenylphosphine) also significantly increased the fluorescence signals.

Copper-Mediated Depropargylation of PPE with Various Cosolvents

Various cosolvents were tested to optimize the copper-mediated depropargylation of PPE. A 1 mM ligand solution of 4-(dimethylamino)phenyl-diphenylphosphine was prepared in DMSO (2.14 mL) and a 15.7 mM solution of $CuSO_4$ was prepared by dissolving 27.8 mg of $CuSO_4$ in Millipore water (11.12 mL). This was then diluted to 10 µM $CuSO_4$ (10 mL) using millipore H2O as the diluent. 8 mM propargyl Pittsburgh Green ether (10 µL) was dissolved in each of the following co-solvents: EtOH, DMSO, NMP, and MeCN (90 µL) in separate 2-mL microcentrifuge tubes. A working solution was prepared for each co-solvent containing: 1.2 M pH 7 phosphate buffer (1.5 mL), the co-solvent (230 µL), 1 mM 4-(dimethylamino)phenyl-diphenylphosphine (20 µL), and 800 µM propargyl Pittsburgh Green ether (50 µL). Each working solution (180 µL) was added to six wells in a black 96-well plate. To the first three wells, Millipore water (20 µL) was added, and 10 µM $CuSO_4$ (20 µL) was added to other three wells. The fluorescence was measured immediately with a Modulus Microplate Multimode plate reader.

Figure 6:
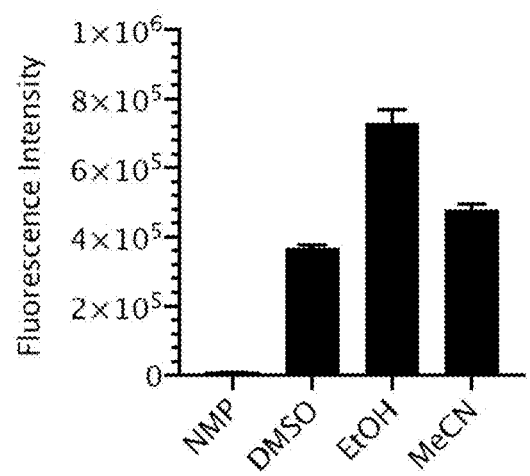
FIG. 6: Effect of cosolvent on copper-catalyzed depropargylation. Conditions: 1 μM $CuSO_4$, 20 μM PPE, 200 μM DMAPPP, 15:85 NMP, DMSO, EtOH, or MeCN:1.2 M phosphate pH 7 buffer, 23° C., 0.5 h, n=3.

Fluorescence intensities (A.U.) of the reactions performed with each cosolvent are shown in FIG. 6. Ethanol was found to interfere with the reaction the least.

Figure 7:
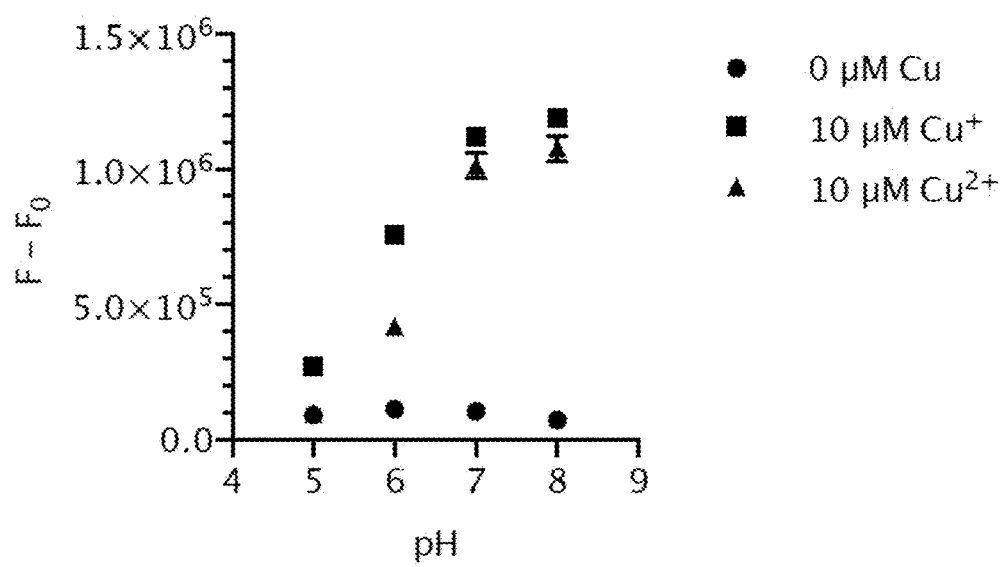
FIG. 7: Effect of pH on reaction. 0 or 10 μM CuCl or $CuCl_2$, 20 μM PPE 200 μM DMAPPP, 1:9 DMSO:50 mM pH 5-8 phosphate buffer, 25° C., 1 h, n=3.

Copper-Mediated Depropargylation of PPE at Varying pH pH 5, pH 6, pH 7, and pH 8 phosphate buffers were purchased from Fisher Scientific and were diluted to 50 mM. Four different working solutions were prepared by mixing the buffers (1.92 mL), DMSO (60 µL), 800 µM PPE in DMSO (60 µL), and 4 mM DMAPPP in DMSO (120 µL). The working solutions (180 µL) were then added to a black 96-well plate. 10 mM CuCl or $CuCl_2$ in 3% HCl was diluted to 100 µM using water as the diluent. These solutions (20 µL) were then added to the wells and the fluorescence was measured. The fluorescence intensity (F-Fo, A.U.) for each reaction is shown in FIG. 7. Phosphate buffer of pH 8 showed the highest fluorescence intensity (A.U.) for the reactions with $Cu^+$ and $Cu^{2+}$.

Copper-Mediated Depropargylation of PPE with Varying Buffers

We also tested the effect of the buffer salt on the reaction. To maintain accessibility of the copper detection method for other laboratories, we chose to test only commercially-available buffers; furthermore, based on our previous results (FIG. 7), we tested only buffers above pH 8. Different buffers were purchased from Fisher Scientific. These were 50 mM phosphate pH 8.5 buffer (Fisher Scientific catalog #SB112-500), 1 M sodium bicarbonate pH 8.5 buffer (Fisher Scientific catalog #AAJ60408AK), 0.5 M borate pH 8.5 buffer (Fisher Scientific catalog #AAJ60803AK), and carbonate pH 10 buffer (Fisher Scientific catalog #AC258605000).

Four different working solutions were prepared by mixing the buffers (1.20 mL), EtOH (184 µL), 800 µM PPE in EtOH (40 µL), and 20 mM DMAPPP in DMSO (16 µL). The working solutions (180 µL) were then added to a black 96-well plate. 0 or 20 M $CuSO_4$ in distilled ultrapure water (20 µL) was then added to the wells and the fluorescence was measured.

Figure 8:
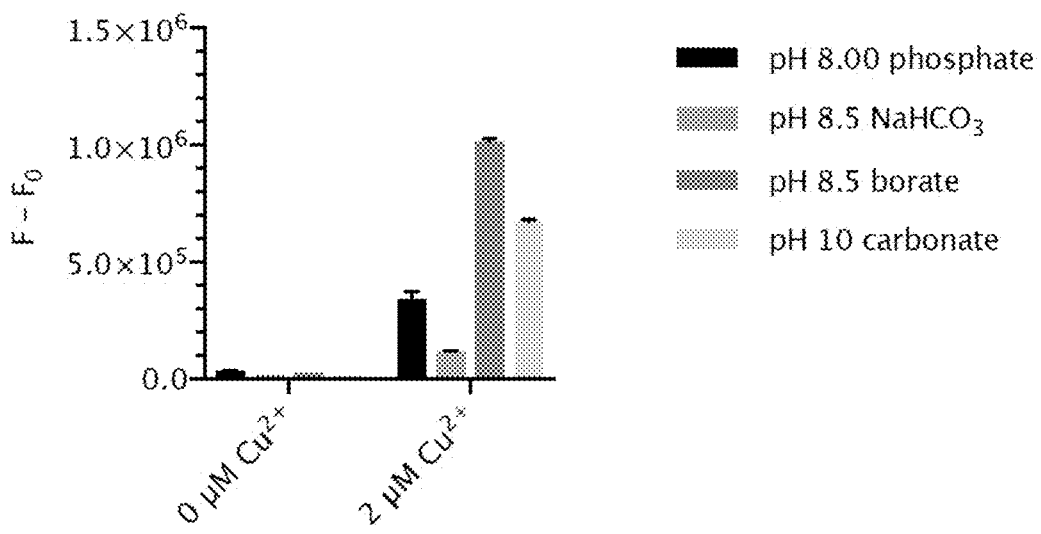
FIG. 8: Effect of buffer salt on reaction. 0 or 2 μM $CuSO_4$, 20 μM PPE, 200 μM DMAPPP, 15:85 EtOH:buffer; 50 mM pH 8.00 phosphate, 1 M pH 8.5 sodium bicarbonate, 0.5 M borate pH 8.5, or pH 10 carbonate buffers, 23° C., 1 h, n=3.

Of the phosphate, bicarbonate, borate, and carbonate buffers we tested, the borate buffer yielded the best result, as evidenced by the highest fluorescence intensity (F-Fo, A.U.) (FIG. 8). By adjusting the buffer concentrations to 50 mM, we determined that the effect observed was due to the identity of the buffer salt and not the concentration of the buffer salts; the carbonate buffer was not tested due to a lack of information from the manufacturer regarding the concentration of the salts. There was no difference in the fluorescence intensities when the borate buffer and phosphate buffer were used at different concentrations, but diluting the bicarbonate buffer significantly increased the fluorescence intensity. Thus, only the bicarbonate buffer was affected by salt concentration.

Figure 9:
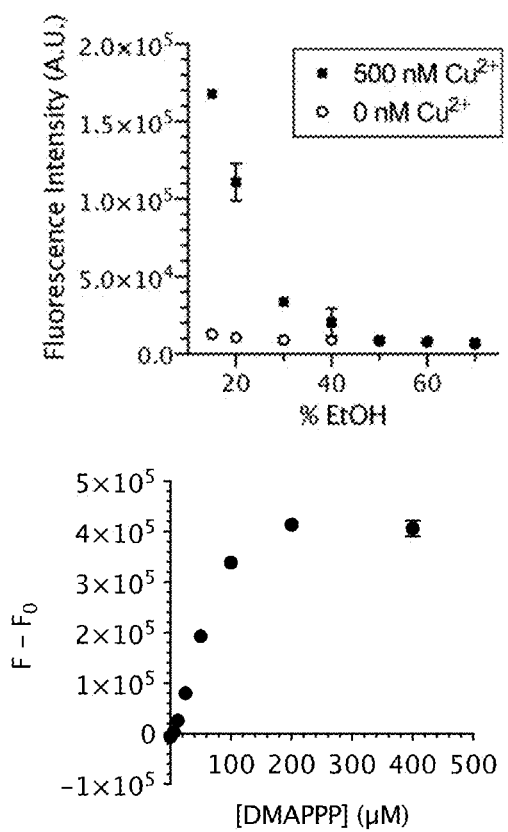
FIG. 9: Effect of DMAPPP concentration. 2 μM $CuSO_4$, 20 μM PPE, 0-400 μM DMAPPP, 15:85 EtOH:1.2 M phosphate pH 7.0 buffer, 25° C., 2 h, n=3.

Copper-Mediated Depropargylation of PPE with Varying Solvent and Ligand Concentrations To further optimize the reaction, we studied the effect of both EtOH and DMAPPP concentration on the rate. To test the effect of solvent concentration, seven different working solutions were prepared, varying only the concentration of EtOH. Solutions containing distilled ultrapure water (1197, 1097, 897, 697, 497, 297, or 97 µL) and EtOH (250, 350, 550, 750, 950, 1150, or 1350 µL) were prepared, to which 500 mM borate pH 8.5 buffer (53 µL), 800 µM PPE in EtOH (50 µL), and 10 mM DMAPPP in DMSO (40 µL) was also added. The working solutions (180 µL) were added to a black 96-well plate. 0 or 5 µM $CuSO_4$ in distilled ultrapure water (20 µL) was then added to the wells and the fluorescence was measured. As the concentration of EtOH was lowered, the rate of the reaction increased, as evidenced by the change in fluorescence intensity (FIG. 9).

To test the effect of ligand concentration, the working solution was prepared by adding 500 mM pH 8.5 borate buffer (2.368 mL), EtOH (400 μL), 800 μM PPE in EtOH (80 μL), and 10 mM DMAPPP in DMSO (32 μL) together. 2× serial dilutions of the working solution were performed using a solution of 800 μM PPE in EtOH (300 μL), DMSO (120 μL), EtOH (1.500 mL), and 500 mM pH 8.5 borate buffer (8.880 mL) as a diluent. Each dilution of the working solution (180 μL) was transferred to a black, round-bottom 96-well plate. The final concentration of the DMAPPP ranged from 0-200 μM.

0 or 5 μM $CuSO_4$ (20 μL) was then transferred to the wells containing the working solution. The fluorescence was measured immediately after the addition of the copper solution, and again after 30 minutes. The fluorescence intensities after 30 min were reported. Average and standard deviation values are shown in FIG. 9.

As the concentration of DMAPPP increased, the reaction rate increased linearly then plateaued at higher concentrations (FIG. 9). 160 μM was then chosen as the ideal concentration of DMAPPP for further studies.

Selectivity of Method to Detect Copper

Following our optimization of the reaction conditions, we revisited the selectivity of the method against other metal ions. The working solution was prepared by mixing 500 mM borate pH 8.5 buffer (13.5 mL), EtOH (2.51 mL), 8.0 mM PPE in EtOH (45 μL), 20 mM DMAPPP in DMSO (144 μL) in a conical tube. The working solution (180 μL) was then added to a black 96-well plate. The metals solutions used for the 2-D screen were then diluted to 10 μM using water as the diluent. The metal solutions (20 μL) were then added to the wells and the fluorescence was measured.

Figure 10:
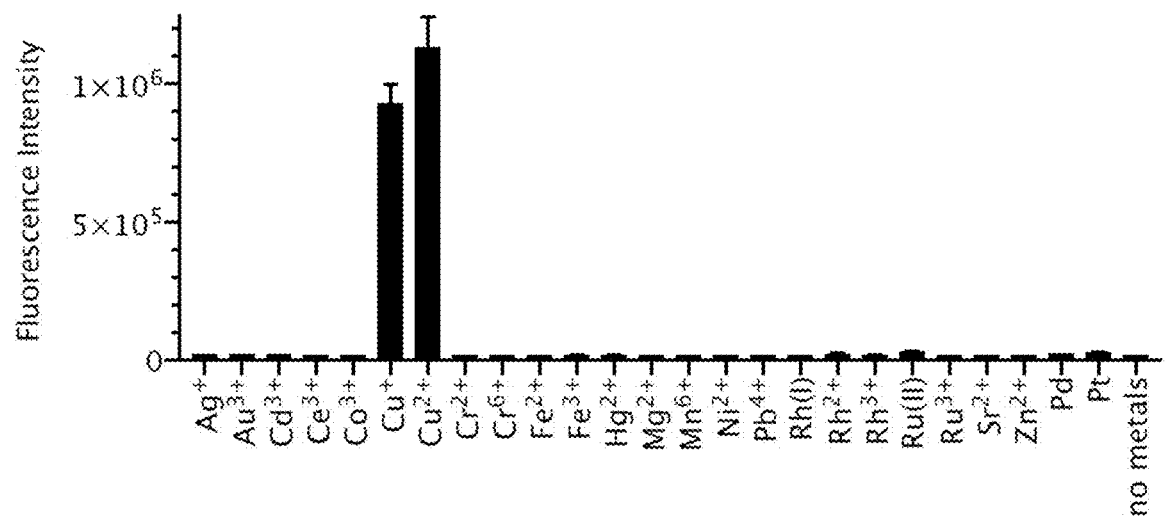
FIG. 10: Metal selectivity of PPE/DMAPPP system. Conditions: 1 μM metals, 20 μM PPE, 160 μM DMAPPP, 15:85 EtOH:500 mM borate pH 8.5 buffer, 26° C., 20 min.

In the presence of 1 μM metals, we observed that only $Cu^+$ and $Cu^{2+}$ could allow the reaction to occur (FIG. 10), as evidenced by the fluorescence intensities (A.U.), indicating that this method is selective for copper.

Determination of Turnover Frequency for Copper-Mediated Depropargylation of PPE

Figure 11:
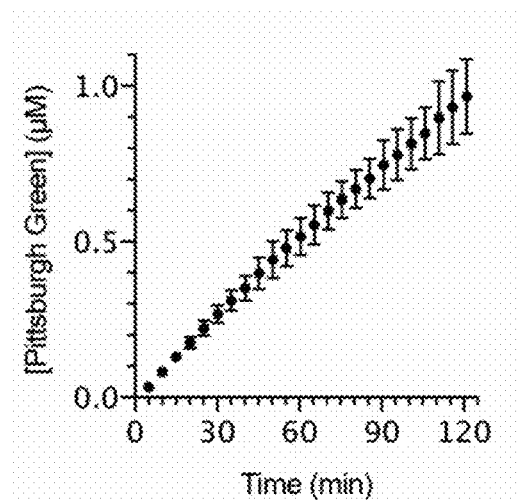
FIG. 11: Kinetic study to determine turnover frequency. Conditions: 200 nM $CuSO_4$, 20 μM PPE, 160 μM DMAPPP, 15:85 EtOH:500 mM borate pH 8.5 buffer, 30° C., n=3.

To determine whether this method was a catalytic method, we monitored the reaction over time (FIG. 11). A standard curve was prepared for dichlorofluorescein (DCF) by dissolving the solid in EtOH to a concentration of 20 mM. The DCF was then diluted to 500 μM in EtOH. A stock solution was prepared by adding 500 mM pH 8.5 borate buffer (600 μL), EtOH (81.6 μL), 500 μM DCF in EtOH (32 μL), 20 mM DMAPPP in DMSO (6.4 μL). This stock solution (200 μL) was then transferred to a black 96-well plate.

The diluent was prepared by mixing 500 mM borate pH 8.5 buffer (9.00 mL), EtOH (1.70 mL), and 20 mM DMAPPP in DMSO (96 μL). The diluent (100 μL) was transferred to the black 96-well plate. 2× serial dilutions were performed by removing 100 μL of the stock solution from the wells and adding it to the wells containing the diluent. Following this, an additional 100 μL of the dilent was added to the wells for a total volume of 200 μL. The fluorescence of these solutions was measured and a standard curve was generated.

The working solution was prepared by mixing 500 mM borate pH 8.5 buffer (1.20 mL), EtOH (187 μL), 800 μM PPE in EtOH (40 μL), 20 mM DMAPPP in DMSO (12.8 μL) in a conical tube. The working solution (180 μL) was then added to a black 96-well plate. 0 or 2.0 μM $Cu^{2+}$ (20 μL) was then added to the wells and the fluorescence was measured every 5 min for 2 h.

The fluorescence value was converted to a concentration of Pittsburgh Green using the linear regression generated from the standard curve of DCF. The fluorescence vs. time was then plotted.

Using 200 nM $Cu^{2+}$ and 20 μM PPE, we determined that after one hour, the reaction product (Pittsburgh Green) was produced at approximately 480 nM concentration (FIG. 11) and continued to be produced. Therefore, the turnover frequency was ~2.4 per hour, indicating that the method was catalytic.

Limit of Detection and Limit of Quantification of Copper-Mediated Depropargylation of PPE We then proceeded to determine the limit of detection (LOD) and limit of quantification (LOQ). The working solution was prepared by adding 500 mM pH 8.5 borate buffer (16.280 mL), EtOH (2.750 mL), 800 μM PPE in EtOH (550 μL), 20 mM DMAPPP in DMSO (120 μL), and DMSO (110 μL) together. The resulting working solution (180 μL) was transferred to a black, round-bottom 96-well plate.

1.11× serial dilutions of $CuSO_4$ in water were performed from 250 nM. The fluorescence was measured immediately after the addition of copper and every five minutes for two hours. The fluorescence intensities at two hours were reported. Average, standard deviation values, and linear regression are shown in FIG. 12.

Figure 12:
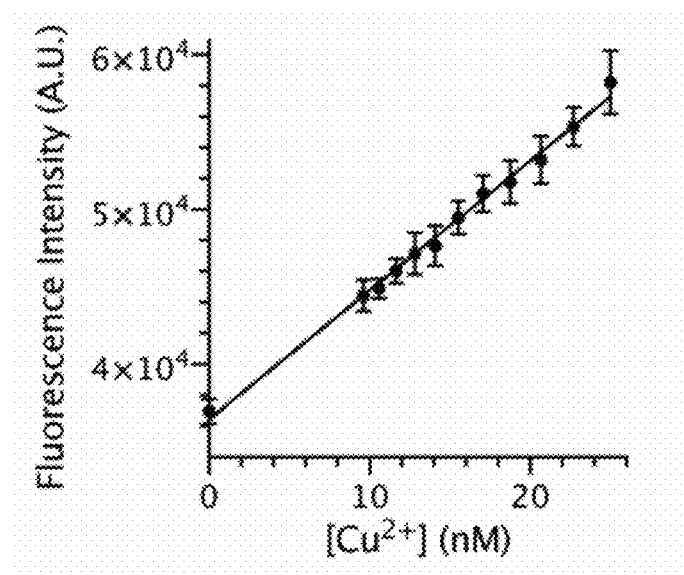
FIG. 12: Copper concentration dependence to determine the limit of detection and limit of quantification. Conditions: 20 μM PPE, 100 μM DMAPPP, 15:85 EtOH:50 mM borate pH 8.5 buffer, 2 h, 25° C., n=8.

After incubating PPE with varying concentrations of copper, we discovered that the relationship between copper concentration and fluorescence intensity was linear (FIG. 12). This kinetic result suggests that the reactive copper species is a monomer under the reaction conditions. After applying a linear regression, the LOD and LOQ were determined to be 4.5 nM and 15.1 nM, respectively, using the standard error of the regression.

Detection of Copper in Drinking Water

We then applied our method to the detection of copper in drinking water. The limit defined by the United States Environmental Protection Agency for the concentration of copper in drinking water is 20 μM.

We obtained three real-world samples consisting of drinking water filtered through a 14-week old water filter, drinking water filtered through a new, unused water filter, and unfiltered drinking water from a water fountain. The working solution was prepared by the addition of 0.5 M borate pH 8.5 (2.10 mL), EtOH (814.5 μL), 800 μM PPE in EtOH (7.5 μL), and 20 mM DMAPPP in DMSO (24 μL). Dowex M4195 resin was added to the working solution. The working solution (500 μL) was transferred to vials. 0 or 5 μM $CuSO_4$ in distilled Milli-Q water or the fountain water samples (500 μL) were added and the fluorescence was observed over time.

Figure 13:
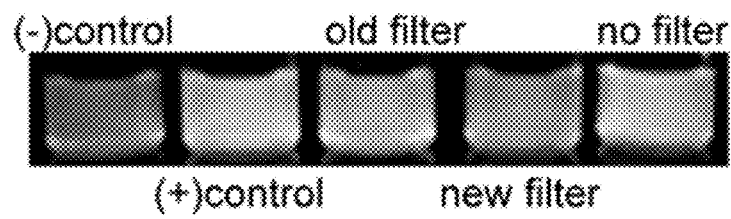
FIG. 13: Visualization of the relative concentrations of copper in drinking water samples.

We compared the drinking water samples with the solutions containing 0 and 5 M $CuSO_4$ in distilled ultrapure water as negative and positive controls, respectively, which showed a marked difference (FIG. 13). Furthermore, we could clearly see that all of the drinking water samples contained copper, with the apparent intensities correlated with whether the sample was filtered and with the age of the filter. The unfiltered water was visibly the most fluorescent of the water samples, followed by the water filtered through the 14-week old filter; the new, unused filter had the lowest fluorescence intensity of the three samples, although it was still more fluorescent than the negative control sample. Importantly, these results suggest that our method can visually detect micromolar concentrations of copper below the government's mandated limit.

Quantification of Copper in Drug-Like Samples

Figure 14:
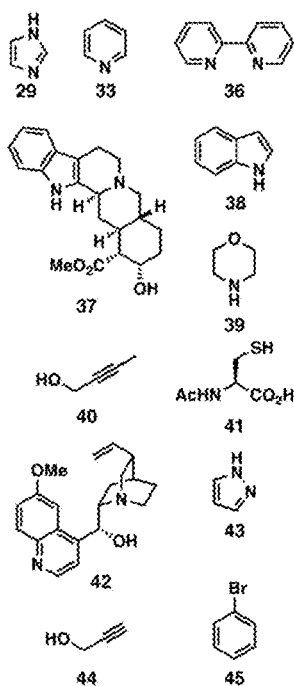
FIG. 14: Structures of compounds used as drug-like samples.

The federal guideline in the United States USP <232> indicates that the copper concentration in the solid state of an active pharmaceutical ingredient (API) must be below 300 parts per millions (ppm). To test whether the fluorometric method can quantify such low concentrations of copper in drug-like material, we chose 12 commercially available functionalized compounds (FIG. 14) containing copper at concentrations of 30 and 300 ppm in the solid phase.

Pyridine, yohimbine, 2,2'-bipyridyl, indole, morpholine, 2-butyn-1-ol, N-acetylcysteine, quinine, imidazole, pyrazole, propynol, and bromobenzene were dissolved in DMSO to a concentration of 10 mg/mL. 10 mg/mL of the drug-like samples (1.00 mL) were mixed with 0.006 or 0.06 mg/mL $CuSO_4$ in water (50 µL).

Distilled Milli-Q water (15.0 µL) was added to the wells of a 96-well plate. 10 mg/mL of 12 different drug-like samples spiked with 0.006 mg/mL $Cu^{2+}$ (5.00 µL) was then added to the wells. The working solution was prepared by the addition of 0.5 M pH 8.5 borate buffer (7.50 mL), EtOH (1.17 mL), 800 µM PPE in EtOH (250 µL), and 20 mM DMAPPP in DMSO (80 µL). The working solution (180 µL) was transferred to the wells and the fluorescence was measured.

Figure 15:
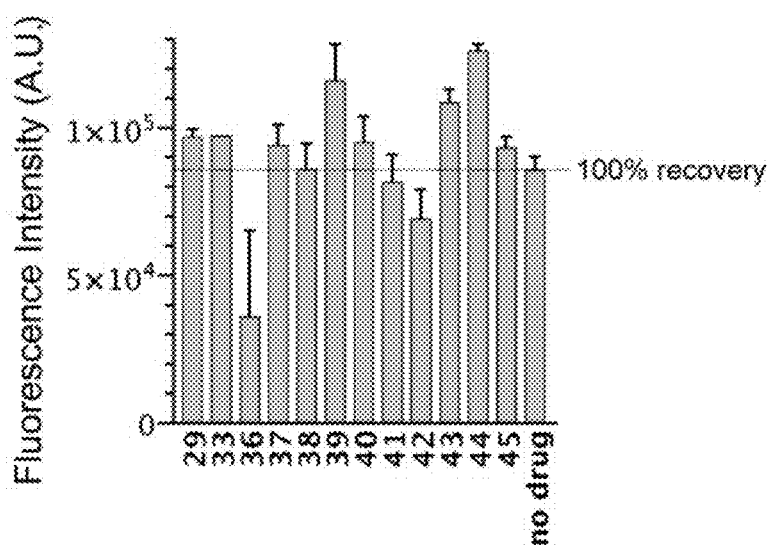
FIG. 15: Quantification of copper in drug-like samples with 30 ppm $Cu^{2+}$. 30 ppm $Cu^{2+}$ in the solid phase, 20 μM PPE, 160 μM DMAPPP, 14.2:3.3:85 EtOH:DMSO:500 mM borate pH 8.5 buffer, 24° C., 1 h, n=3.
Figure 16:
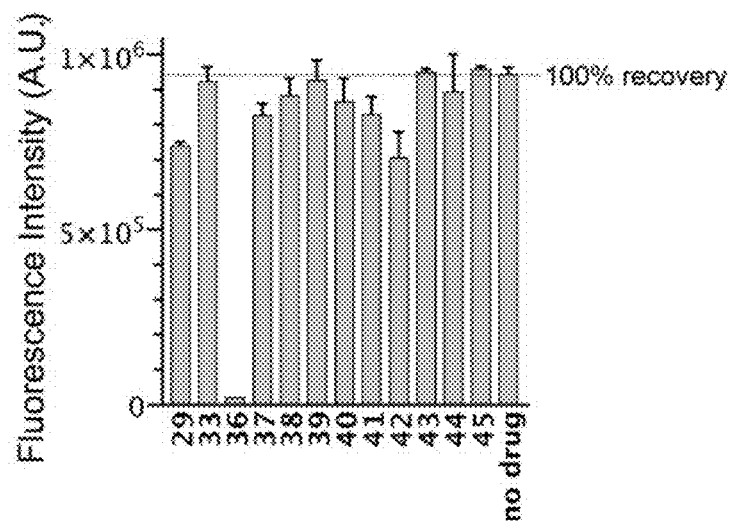
FIG. 16: Quantification of copper in drug-like samples with 300 ppm $Cu^{2+}$. 300 ppm $Cu^{2+}$ in the solid phase, 20 μM PPE, 160 μM DMAPPP, 14.2:3.3:85 EtOH:DMSO:500 mM borate pH 8.5 buffer, 24° C., 1 h, n=3.

With the final copper concentrations of 7.1 or 71 ng mL$^{-1}$ in the assay solution, the fluorescence intensity correlated with the positive control ("no drug" in FIGS. 15 and 16) despite the presence of the drug-like compounds; the only exception to this was with 2,2'-bipyridyl (36), which interfered with the method. Excluding the 2,2'-bipyridyl (36), the average percent recoveries for the samples with 30 and 300 ppm copper were 112±19% and 92±10%, respectively. These results were consistent across repeated experiments. This result indicates that the method may be applied in the pharmaceutical process chemistry. We compared our method with ICP-OES for imidazole (29) and 2,2'-bipyridyl (36); although ICP-OES was able to determine copper concentrations in the 300 ppm samples, it failed to quantify the metal in the corresponding 30 ppm samples. Thus, although ICP-OES may be more robust in the presence of strong metal chelators due to sample preparation through acid digestion, our method is more sensitive than ICP-OES.

Copper-Mediated Depropargylation for Biological Samples

To develop a fluorescence imaging method for intracellular copper ions, we compared the reaction under our optimized system to that which we would apply for cellular imaging. Two working solutions were prepared by mixing 500 mM borate pH 8.5 buffer or HBSS (1.20 mL), ethanol (223 µL), 8.0 mM PPE in ethanol (4.00 µL), and 20 mM DMAPPP in DMSO (12.8 µL). The working solutions (180 µL) were transferred to a black 96-well plate and 0 or 5 M $CuSO_4$ in water (20 µL) was added. The fluorescence was then measured every 10 min for 1 h at room temperature (23° C.).

Figure 17:
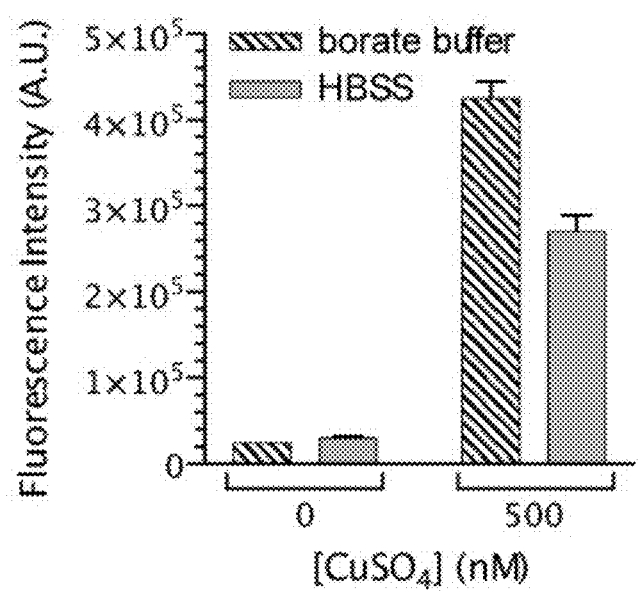
FIG. 17: Comparison of buffer. 0 or 500 nM $CuSO_4$, 20 μM PPE, 160 μM DMAPPP, and 15:85 EtOH:500 mM borate pH 8.5 buffer or 1:99 DMSO:HBSS.

Reducing the cosolvent concentration to 1% and using Hank's Balanced Salt Solution (HBSS) as the buffer resulted in a signal that was approximately 60% of that under optimized conditions (FIG. 17). This would be sufficient to observe a difference in fluorescence intensity under cellular conditions.

We questioned whether copper ions would be excreted from cells when bound to DMAPPP. As a model system, $CuSO_4$ was suspended in a biphasic system (pH 7 buffer and $CHCl_3$) in the presence or absence of DMAPPP. Three suspensions were prepared from these: 10 mM DMAPPP in $CHCl_3$ (1.0 mL) and 5 mM $CuSO_4$ in 1 mM phosphate pH 7.0 buffer (1.0 mL), $CHCl_3$ (1.0 mL) and 5 mM $CuSO_4$ in 1 mM phosphate pH 7.0 buffer (1.0 mL), and 10 mM DMAPPP in $CHCl_3$ (1.0 mL) and 1 mM phosphate pH 7.0 buffer (1.0 mL). The suspensions were vortexed to ensure proper partitioning of the $CuSO_4$ and DMAPPP. Aliquots of the aqueous and organic layers of each suspension (100 µL each) were then taken and evaporated. The residue following evaporation was resuspended in HBSS (100 µL).

The working solution was prepared by the addition of 50 mM pH 8.5 borate buffer (2.96 mL), EtOH (500 µL), 800 µM PPE in EtOH (100 µL), and 10 mM DMAPPP in DMSO (40 µL). The working solution (180 µL) was transferred to the wells of a black 96-well plate. The resuspended samples (20 µL) were then added to the wells and the fluorescence was measured.

Figure 18:
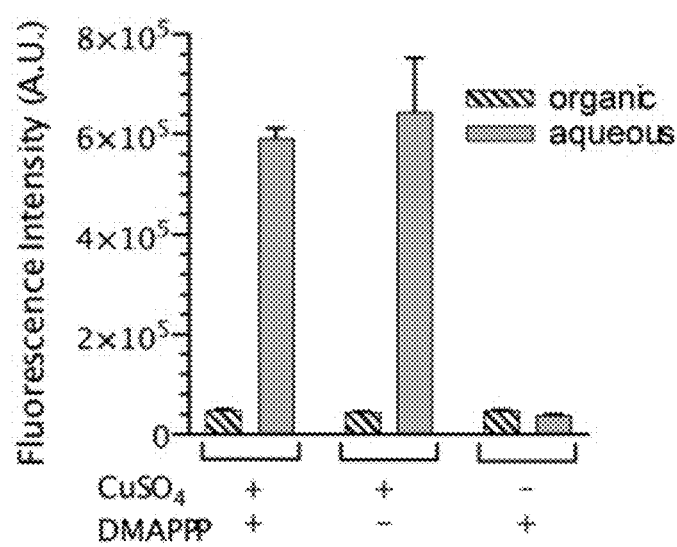
FIG. 18: Distribution of copper between water and $CHCl_3$ in the presence of DMAPPP. Organic layer, aqueous layer (pH 7), 0 or 5 μM $CuSO_4$ in $H_2O$, 20 μM PPE, 160 μM DMAPPP, 15:85 EtOH:500 mM borate pH 8.5 buffer, 1 h, 25° C., n=3.

To our surprise, the copper concentrations did not increase in the organic phase when DMAPPP was present (FIG. 18), indicating that the putative copper-DMAPPP complex may not be membrane-permeable or may not be sufficiently stable.

Finally, we applied our method to imaging cellular pools of copper. HeLa cells were loaded with 1 mM $CuSO_4$ in DMEM for 30 min at 37° C. The cells were washed. PPE and DMAPPP were added during imaging to a final concentration of 20 M and 160 µM, respectively. Images were obtained on a Nikon Ti microscope equipped with a 60× (1.4 NA) objective.

Figure 19:
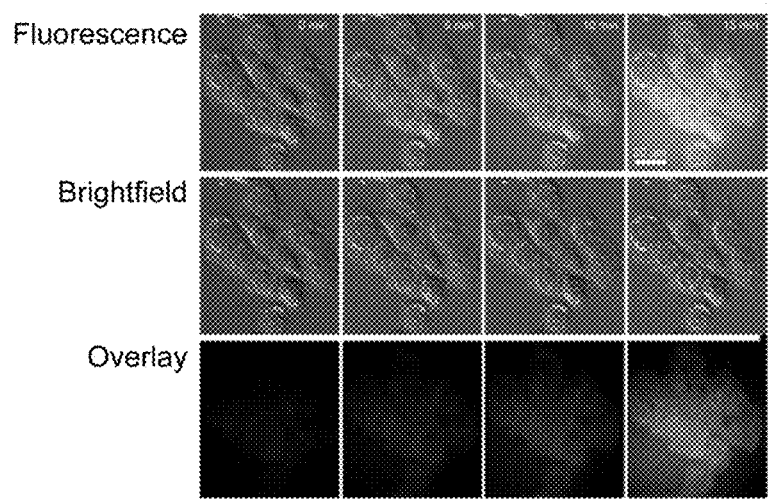
FIG. 19: Fluorescence imaging of copper ions in live cells. Final: 1 mM $CuSO_4$, 20 μM PPE, 160 μM DMAPPP.

A time-dependent increase in fluorescence was observed within cells over the course of 15 min (FIG. 19). At the 15-min time point, fluorescence was observed outside of the cells; we attribute this to the diffusion of Pittsburgh Green. Our results here suggest that cellular copper pools can be observed with our method, among the other applications previously described.

Deallylation of Fluorochrome with Various Metals and Ligands

Metals and ligands were combinatorially screened in the presence of allyl Pittsburgh Green ether (APE) to determine which metals and ligands facilitated the deallylation reaction.

Commercially available Ligands (1-36, FIGS. 1A and 1B) used in the screen included tri-o-tolylphosphine, 3-(diphenylphosphino)bezenesulfonic acid sodium salt, 1,3,5-triaza-7-phosphaadamantane, 1,1'-bis(diphenylphosphino)ferrocene, tri(2-furyl)phosphine, 1,2-bis(diphenylphosphino) ethane, bis(4-carboxyphenyl)(4-trifluoromethylphenyl) phosphine, tris(2,4-di-tert-butylphenyl)phosphite, 4-(dimethylamino)phenyl-diphenylphosphine, 1,4-bis(diphenylphosphino)butane, 1,3-bis(diphenylphosphino)propane, bis(3-sulfonatophenyl)(3,5-di-trifluoromethylphenyl) phosphine disodium salt, tris(4-fluorophenyl)phosphine, (±)-2,2'-bis(diphenylphosphino)-1,1'-binapthyl, tris(4-methoxyphenyl)phosphine, 2-(di-tert-butylphosphine)biphenyl, (1R,2R)-(+)-1,2-diaminocyclohexane-N,N'-bis(2-diphenylphosphino-1-naphthoyl), tri-p-tolylphosphine, tris (4-trifluoromethylphenyl)phosphine, triphenylphosphine-3, 3',3"-trisulfonic acid trisodium salt, tri-tert-butylphosphonium tetrafluoroborate, bis (diphenylphosphino)methane, di-tert-butylmethylphosphonium tetrafluoroborate, bis(2-diphenylphosphinophenyl)ether, tris(2-cyanoethyl) phosphine, thymine, 2-amino-1,3-propanediol, cytosine, imidazole, 1,3-diphenylthiourea, thiophene, thiazole, pyridine, triphenylphosphine, indole-3-carboxylic acid, and 2,2'-bipyridyl.

In separate vials, ~20-30 mg of each ligand was dissolved in DMSO containing 250 ppm butylated hydroxyl toluene (BHT) to a final concentration of 20 mM ligand. Working solutions containing the ligands were prepared by mixing 1.23 M pH 7 phosphate buffer (177.2 mL), DMSO (19.424 mL), and 8.0 mM APE in DMSO (556 µL). Aliquots of this mixture (4.944 mL) were placed into 15 mL conical tubes and 20 mM ligands and 250 ppm BHT in DMSO (55.5 µL) were added. Aliquots of these working solutions (180 µL) were added to black round-bottom 96-well plates.

Metals used in the experiments included $AgNO_3$, $AuCl_3$, $CdCl_2 \cdot 2.5H_2O$, $CeCl_3 \cdot 3H_2O$, $CoCl_2 \cdot 6H_2O$, $CrCl_2$, $Na_2Cr_2O_7$, $CuCl$, $CuCl_2 \cdot 2H_2O$, $FeSO_4$, $FeCl_3$, $HgCl_2$, $MgCl_2 \cdot 6H_2O$, $K_2MnO_4$, $NiCl_2$, $Pb(OAc)_2$, $RhCl(PPh_3)_3$, $Rh(OAc)_2$ dimer, $RhCl_3 \cdot xH_2O$ (45.5% Rh), dichloro(p-cymene)ruthenium(II), $RuCl_3$, $Sr(NO_3)_2$, and $ZnCl_2$.

In separate vials, 10 mM metal solutions were prepared by mixing ~5-20 mg of the listed metals with dilute acid; all metals were dissolved in 3% HCl (TraceMetal Grade), with the exception of $AgNO_3$, $Sr(NO_3)_3$, $RhCl(PPh_3)_3$, and dichloro(p-cymene)ruthenium(II). $AgNO_3$ and $Sr(NO_3)_3$ were dissolved in 5% $HNO_3$ (TraceMetal Grade); $RhCl(PPh_3)_3$ and dichloro(p-cymene)ruthenium(II) were dissolved in DMSO and the working solutions were adjusted to account for the solvent. The metal solutions were then diluted to 100 µM in 3% HCl or 5% $HNO_3$ (TraceMetal Grade) or DMSO.

100 µM $Pd^{2+}$ and $Pt^{2+}$ solutions were prepared by diluting Pd and Pt standard solution (1000 ppm=9.4 mM or 5.1 mM for Pd and Pt, respectively). For Pd, the 9.4 mM standard (21 µL) was added to 5% $HNO_3$ (1.98 mL, TraceMetal Grade). For Pt, the 5.1 mM standard (39 µL) was added to 3% HCl (1.96 mL, TraceMetal Grade).

Figure 20:
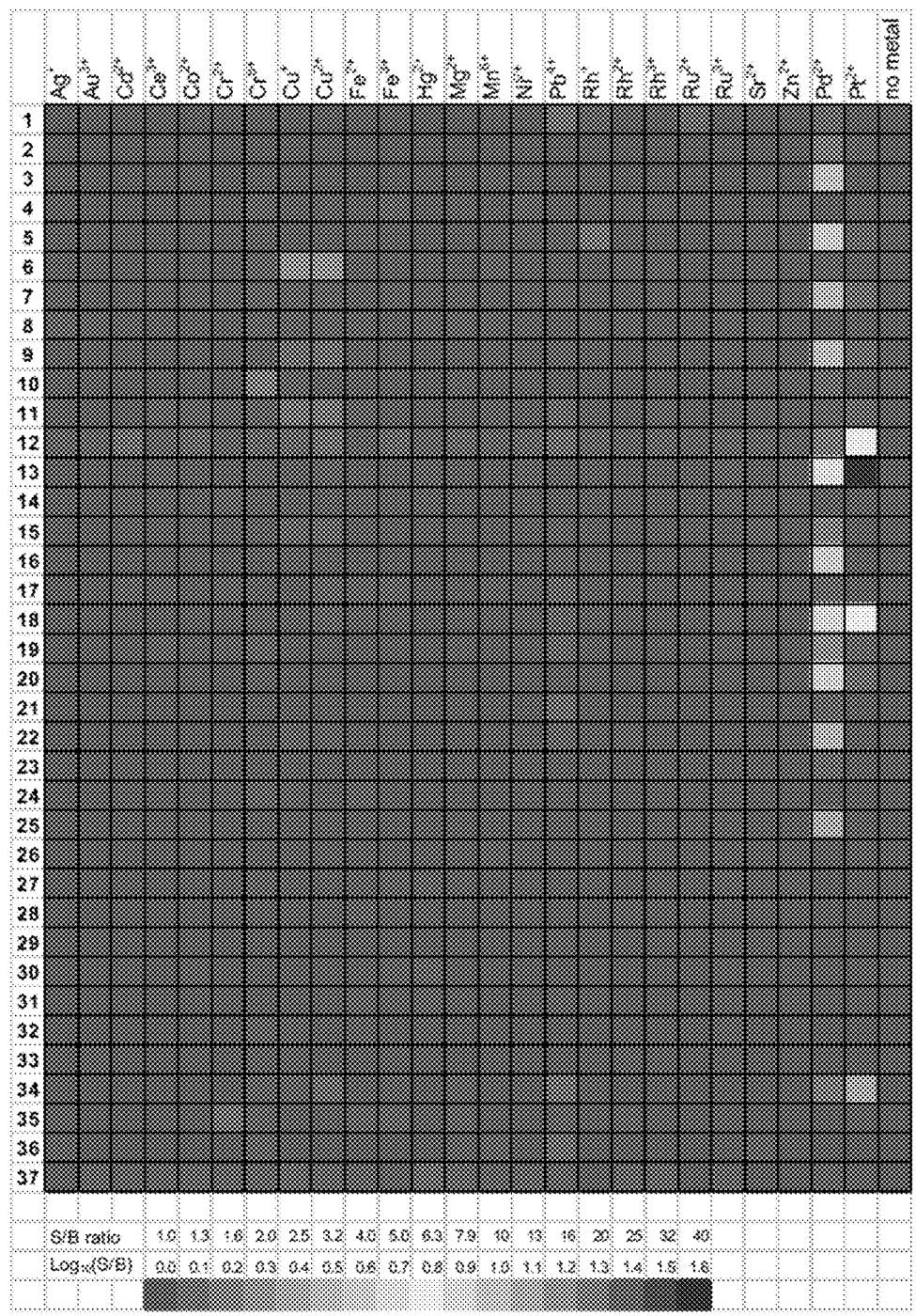
FIG. 20: Heat map of ligand vs. metal screen using APE with ligand. Row 37 contains no ligand.

To perform the assay, 10 µM metal solutions (20 µL) were added to the prepared working solutions (180 µL). The fluorescence was measured immediately and again after allowing the reaction to proceed for 1 h and 2 h at 25° C. FIG. 20 shows a heat map with signal-to-background (S/B) ratios of fluorescence intensity.

The fluorescence signal from the reaction of $Pt^{2+}$ and APE in the presence of tris(4-fluorophenyl)phosphine (TFPP, 13) was the most prominent, in which the signal was 40-fold higher than the background signal and 10-fold higher that the corresponding signal from $Pd^{2+}$. Because palladium is generally the most effective metal for allylic C—O bond cleavage, it is striking that TFPP rendered platinum the most reactive metal for such cleavage. Other metals did not produce Pittsburgh Green in the presence of TFPP.

TFPP (13), 12, and 18 also facilitated the deallylation, with TFPP generating superior signal intensity. Three phosphines 13, 18, and 34 only differ in the para substituents (F, $CH_3$, and H, respectively). Surprisingly, para-substituted phosphines 15 and 19 ($OCH_3$ and $CF_3$, respectively) did not facilitate the deallylation, suggesting that specific para-substituents are required. None of the bidentate phosphines facilitated the deallylation of APE. With 200 µM TFPP, this new catalysis was 4 times faster than the previously reported Pt-$Ph_3$P catalysis.

Selectivity of Method to Detect Platinum

Figure 21:
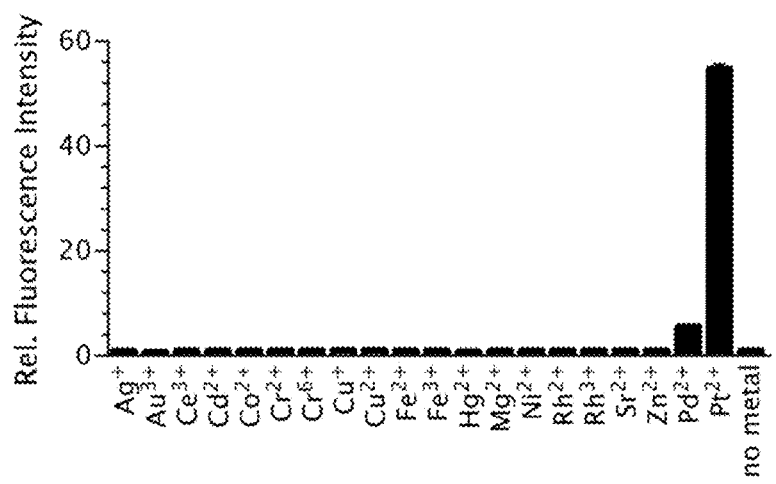
FIG. 21: Relative reactivities of metals (10 μM) to APE with TFPP. 20 μM APE, 200 μM TFPP, pH 7.8, 25° C., 10 min, n=3.

Following optimization of the salts present, pH, and TFPP concentration, the optimized method was 14 times more selective for platinum over palladium (FIG. 21). Increased temperatures accelerated the deallylation, opening an avenue for even lower detection limits if necessary.

Establishing a Pt Standard Curve

The working solution was prepared by adding 1.2 M pH 7.8 phosphate buffer (17.72 mL), 800 µM APE in DMSO (556 µL), 40 mM TFPP and 250 ppm BHT in DMSO (222 µL), and DMSO (1.44 mL) together. The resulting working solution (180 µL) was transferred to black round-bottom 96-well plates.

Figure 22:
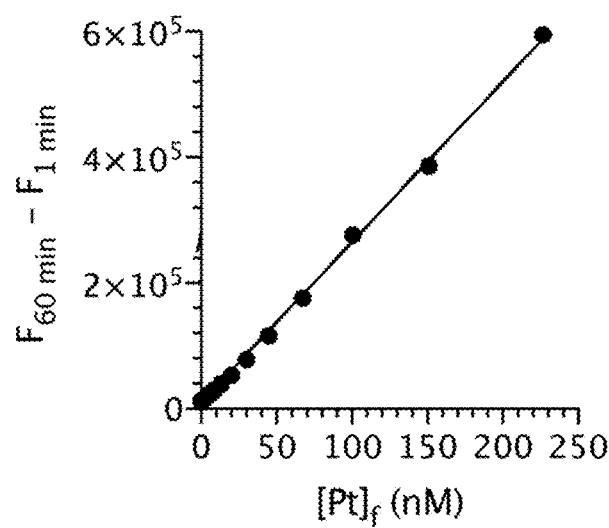
FIG. 22: Standard curve for Pt. 20 μM APE, 400 μM TFPP, pH 7.8, 25° C., 1 h, n=3.

1.5× serial dilutions of the Pt standard were performed from 5.1 M in 0.3% HCl using ultrapure water as the diluent. The Pt solutions (20 µL) were then transferred to the wells containing the working solution. The fluorescence was measured immediately after the addition of the platinum solutions and again after incubation at 25° C. for 1 h. The difference in the fluorescence intensities was reported. Average, standard deviation values, and linear regression are shown in FIG. 22.

Figure 23:
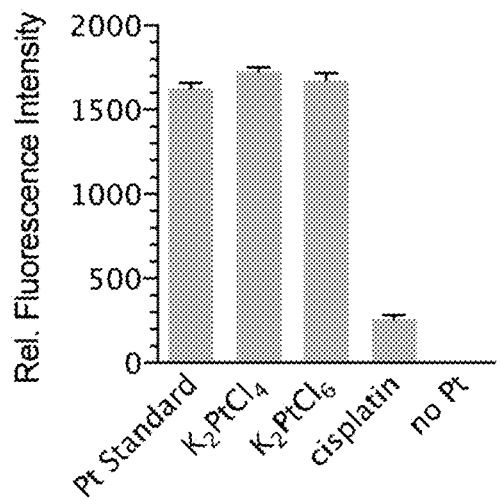
FIG. 23: Relative reactivity of various platinum species. 20 μM APE, 400 μM TFPP, pH 7.8, 25° C., 10 min. n=3.

FIG. 23 shows that the method is quantitative. The limit of quantification (LOQ) and limit of detection (LOD) of the method, with 1 h incubation, based on the standard error of the regressions were 18.3 nM and 5.5 nM, respectively. Since the method is a catalysis-based method, allowing the reaction to proceed for longer periods of time would lower the LOQ and LOD. We also assessed whether the method could accurately determine the concentrations of unknown samples. In a double-blind format, we treated platinum samples in the same manner as the samples for FIG. 24. The concentrations of platinum were known to those who prepared the samples, but not known to the authors. We then generated a linear regression and determined the percent recovery of the unknowns. Percent recoveries (100%× experimental value/theoretical value) ranged from ~90-115% in 4 of 6 samples, indicating that this method may be sufficiently accurate.

Determination of Platinum Concentrations in Rock Extracts

We applied this method to determine platinum content in the presence of several metals native to a rock extract. The rock sample (77.8 mg), containing negligible amounts of platinum and palladium, was measured into a glass vial. Aqua regia (4.00 mL) was then added and the mixture was stirred for 18 h at 25° C. to extract the metals from the rock. The extraction was then quenched by the addition of ultrapure water (16.0 mL).

A Pt standard solution was diluted to a concentration of 2.24 µM using the rock extract as a diluent; a Pd standard solution was diluted to a concentration of 11.54 µM using the rock extract as a diluent. The solutions were mixed together in a 1:1 ratio; this mixture was then diluted 2×. 0-10 µM of Pt or Pd standard in distilled Milli-Q water (20 µL) or the diluted Pt/Pd containing rock extract (20 µL) was added to the wells of a black 96-well plate.

The Pt working solution was prepared by the addition of 1.2 M phosphate pH 7.8 buffer (6.4 mL), DMSO (520 µL), 800 µM APE in DMSO (200 µL), and 40 mM TFPP in 250 ppm BHT in DMSO (80 µL). The working solution (180 µL) was transferred to the wells and the fluorescence was measured.

Using the fluorescence method of the present disclosure, the concentration of platinum in the sample was calculated to be 1.12 µM. This result indicated that despite the high concentration of other metals in rock samples (e.g. palladium, iron, magnesium, aluminum, etc.), the method could still accurately quantify trace platinum in these samples. Furthermore, palladium did not interfere with the reaction and the method was selective enough to be used in the metallurgy of platinum ores.

Detection of Platinum in Different Oxidation States

To determine whether our method depends on the oxidation state of platinum, we incubated the solution of APE and TFPP with a platinum(II) standard, $K_2PtCl_4$, $K_2PtCl_6$, or cisplatin for 10 min. Cisplatin (6.1 mg; 20 µmol) was dissolved in DMSO and diluted to a concentration of 10 µM.

K₂PtCl₄ (5.6 mg; 13 μmol) and K₂PtCl₆ (6.8 mg; 14 μmol) were dissolved in water to a concentration of 10 μM. The Pt standard was diluted with ultrapure water to a concentration of 10 μM. The working solution was prepared by adding 1.2 M pH 7 phosphate buffer (8.86 mL), 800 μM APE in DMSO (278 μL), 20 mM TFPP and 250 ppm BHT in DMSO (111 μL), and DMSO (721 μL) in a 15-mL conical tube. The working solution (180 μL) and the Pt solutions (20 μL) were transferred in this order to black round-bottom 96-well plates. The reaction mixture was incubated at 25° C. for 1 h before the fluorescence was measured and reported. Average values and standard deviations are shown in FIG. 23 and "no Pt" is normalized to 1.

The first three platinum species showed similar fluorescence signals (FIG. 23), suggesting that total platinum concentrations can be measured regardless of the oxidation state under the reaction conditions. Pt(IV) is likely reduced to Pt(II) by TFPP, as platinum reduction of phosphines is known. Cisplatin exhibited reactivity, although it was lower than the inorganic species. Addition of NaBH₄ to the Pt(II) solution did not increase the signals.

Quantification of Cisplatin

To test whether our method can quantify clinically relevant, protein-free platinum, we precipitated proteins from serum and spiked the serum with cisplatin. Protein-free serum was prepared by mixing 1:2 serum to ethanol. The mixture was centrifuged at 14,000 rpm in an Eppendorf Centifuge 5417R for 1 h at 4° C. Cisplatin (5.0 mg, 17 μmol) was dissolved in DMSO (1.67 mL) to generate a 10 mM solution; this solution was diluted to a concentration of 1.0 mM. The cisplatin solution was added to protein-free serum in a 1:999 v/v ratio, resulting in a final concentration of 1.0 μM cisplatin in protein-free serum. 1.11× serial dilutions were performed using this sample as the highest concentration and protein-free serum as the diluent. The working solution was prepared in the same way as in the standard curve experiment. The working solution (180 μL) was added to the cisplatin-serum samples (20 μL) in black round-bottom 96-well plates, and the fluorescence was measured immediately. Following the initial measurement, the plates were covered to prevent evaporation and incubated at 45° C. for 1 h before measuring the fluorescence again. The difference in fluorescence intensities was reported.

Figure 24:
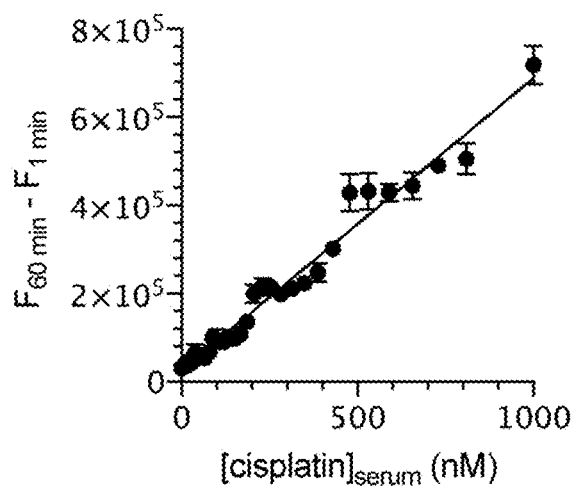
FIG. 24: Standard curve of cisplatin in serum. 400 μM TFPP, 20 μM APE, pH 7.8, 45° C., 1 h, n=6.

We observed a linear correlation between cisplatin concentration and fluorescence intensity (FIG. 24). The LOQ and LOD of the method based on the standard error of the regression were 410 and 120 nM, respectively, which is comparable to atomic emission spectroscopy (LOD ~260 nM platinum in sera).

Detections of Platinum in Biological Samples

We then applied this method for cellular imaging. HeLa cells were seeded in 35-mm dishes and were incubated overnight in an incubator (37° C., 5% CO₂ atmosphere) in DMEM supplemented with 10% bovine calf serum and 1% penicillin/streptomycin. Cells were loaded with APE and TFPP to a final concentration of 1 μM and 200 μM, respectively, in 1% DMSO in DMEM for 20 min. Following this, cells were washed twice with ~2 mL HBSS. HBSS was used as the imaging medium. Brightfield images were taken, as well as the initial fluorescence image. Immediately after taking the first fluorescence image, a solution of K₂PtCl₄ in PBS was added to a final concentration of 1 mM.

Cellular images were taken using an Olympus IX81 microscope with a 10× objective. Brightfield images were taken using a 3 ms exposure. Fluorescence images were taken as a time series, with an image taken every 30 s for 20 min, using an 850 ms exposure. Images were processed using ImageJ software; background fluorescence was removed from the fluorescence images using a rolling ball radius of 50.0 pixels.

Figure 25:
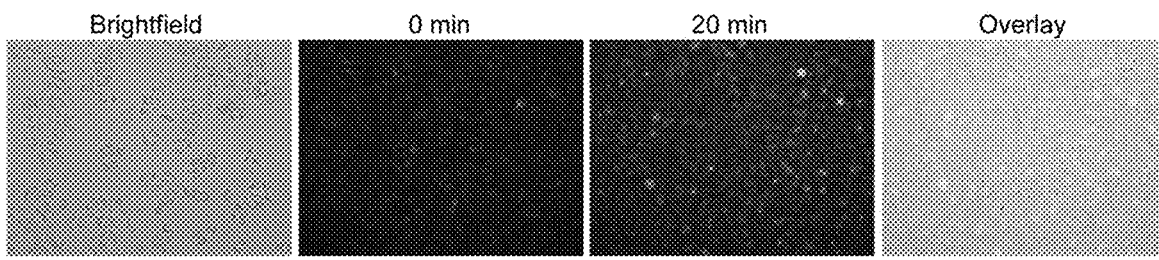
FIG. 25: Fluorescence imaging of platinum in live HeLa cells. 1.0 mM $K_2PtCl_4$ in PBS, 1 μM APE, 200 μM TFPP, 1% DMSO in HBSS, 25° C., 20 min.

Over the course of 20 min, fluorescence intensity increased 1.5-fold despite the diffusion of Pittsburgh Green (FIG. 25), indicating that this method is applicable to cellular imaging of platinum.

Detection of Strongly-Ligated Platinum Drugs

Figure 26:
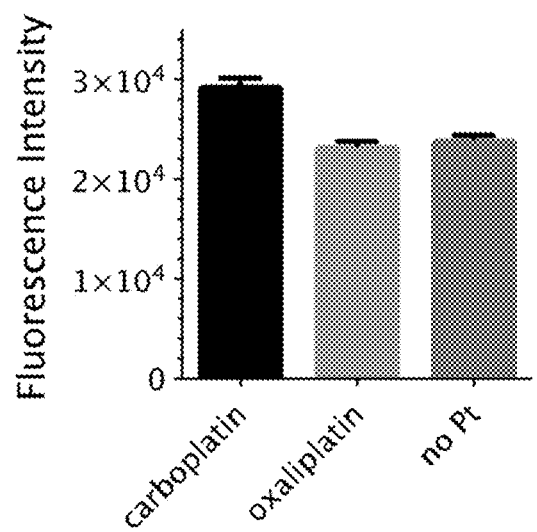
FIG. 26: Reactivity of platinum drugs with APE. Final: 0 or 10 μM carboplatin or oxaliplatin, 20 μM APE, 400 μM TFPP, 10% or 20% DMSO in 1.2 M phosphate pH 7.8 buffer, 45° C., 1 h, n=3.

We incubated carboplatin and oxaliplatin with APE and TFPP. However, even with temperature increased to 45° C., we saw little reaction with these platinum species compared to a sample containing no platinum (FIG. 26). Carboplatin and oxaliplatin were dissolved in DMSO. The solutions were diluted to a concentration of 100 M in DMSO. 100 μM platinum drugs in DMSO or water (20 μL) were transferred to the wells of a black 96-well plate. The working solution was prepared by the addition of 1.2 M phosphate pH 7.8 buffer (17.60 mL), DMSO (1.43 mL), 800 μM APE in DMSO (550 μL), and 40 mM TFPP in 250 ppm BHT in DMSO (220 μL). The working solution (180 μL) was then transferred to the wells and the initial fluorescence was measured. The plate was then covered and allowed to incubate in a 45° C. oven for 1 h before the fluorescence was measured again.

We pre-incubated the drugs with either LiCl or NaCl before adding APE and TFPP.0 or 100 μM cisplatin, carboplatin, or oxaliplatin in DMSO (100 μL) were added to centrifuge tubes. To these tubes, 0 or 1 M LiCl or NaCl in water (100 μL) was added. The solutions were then allowed to incubate at room temperature for 4 h. The working solution was made by the addition of 1.2 M phosphate pH 7.8 buffer (8.86 mL), DMSO (721 μL), 800 μM APE in DMSO (278 μL), and 20 mM TFPP in 250 ppm BHT in DMSO (111 μL). The working solution (180 μL) was then transferred to the wells of a black 96-well plate. The platinum drugs (20 μL) were then transferred to the wells and the fluorescence was measured every 5 min for 100 min.

Figure 27:
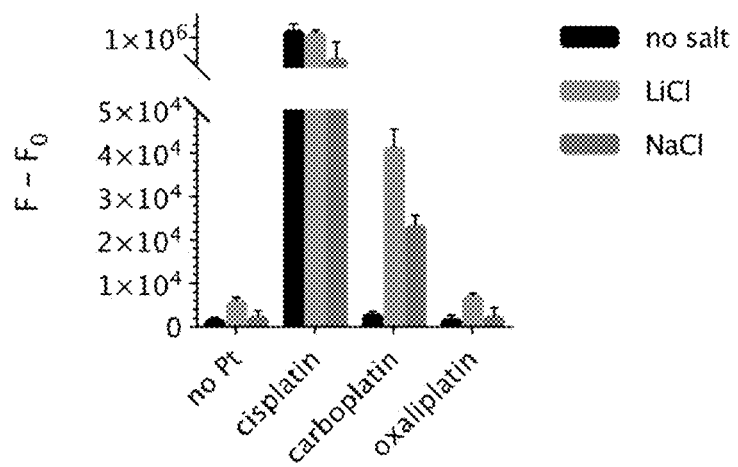
FIG. 27: Reactivity of platinum drugs after pre-incubation with LiCl or NaCl. Final: 0 or 10 μM cisplatin, carboplatin, or oxaliplatin, 0 or 50 mM LiCl or NaCl, 20 μM APE, 400 μM TFPP, 15% DMSO in 1.2 M phosphate pH 7.8 buffer, 25° C., 100 min, n=4.

The LiCl and NaCl addition allowed us to detect carboplatin, as observed by the increased fluorescence of carboplatin samples containing salt versus that without salt; this suggests that excess chloride was able to displace the bis-carboxylate ligand from the platinum center (FIG. 27). Pre-incubation with chloride did not improve the detection of oxaliplatin, known to be exceptionally stable. Pre-incubation did not improve the detection of cisplatin, likely because the added chloride would simply displace the chloride ligands already bound to the platinum center.

Because carboplatin and oxaliplatin are much more stable compared to cisplatin, we tested if reducing the platinum center to Pt(0), thereby causing the degradation of drug, would allow us to detect platinum. As such, we added varying concentrations of cisplatin, carboplatin, and oxaliplatin to a mixture of APE, TFPP, and NaBH₄. 0-10 μM cisplatin, carboplatin, or oxaliplatin in water (20 μL) were added to the wells of a black 96-well plate. The working solution was prepared by the addition of 1.2 M phosphate pH 7.8 buffer (53.16 mL), DMSO (666 μL), 800 μM APE in DMSO (1.668 mL), and 40 mM TFPP in 250 ppm BHT in DMSO (666 μL). 2.5 M NaBH₄ in 10 M NaOH (150 μL) was added to the working solution immediately before adding the working solution to wells; the working solution (180 μL) was then transferred to the wells of a black 96-well plate and the fluorescence was measured every 5 min for 100 min.

Figure 28:
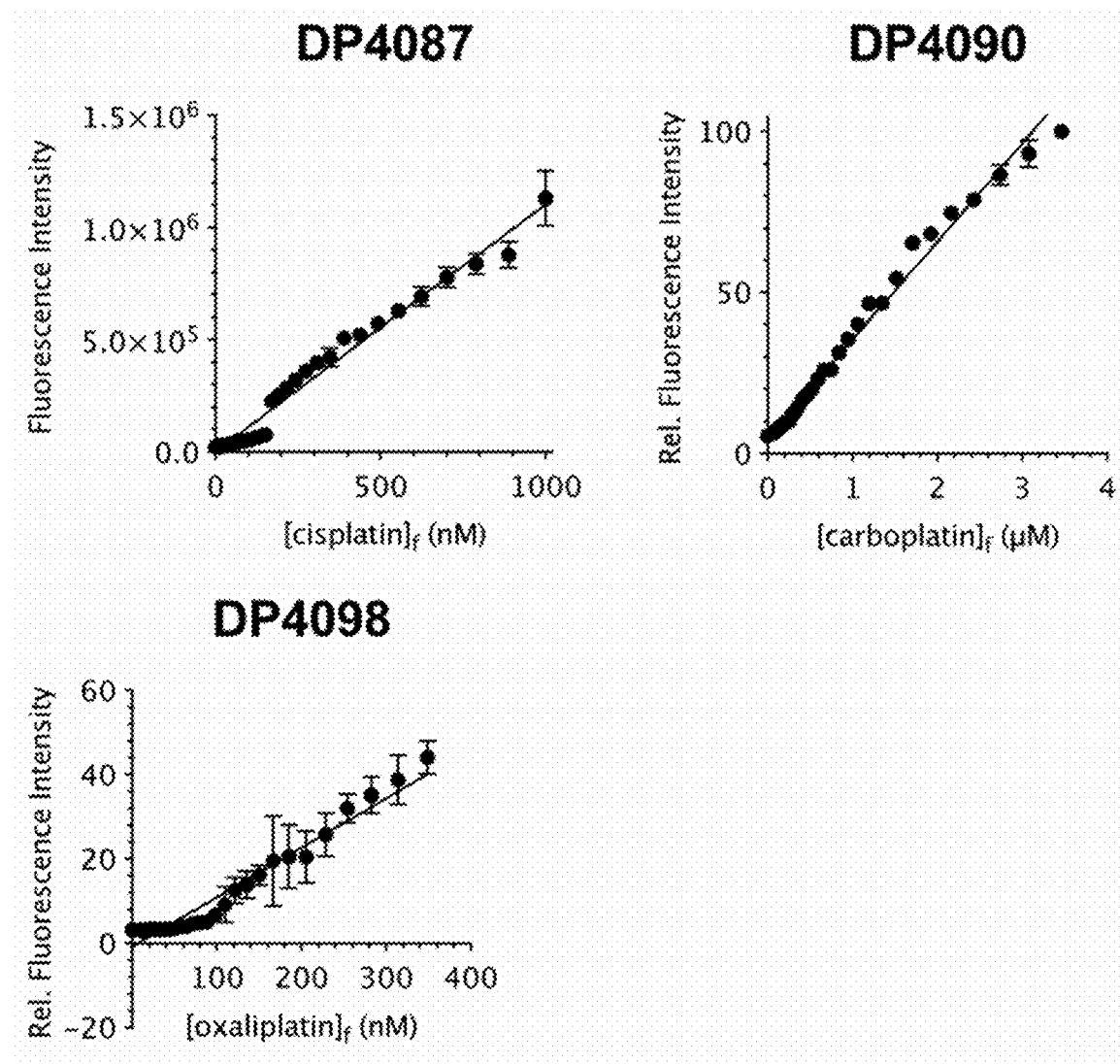
FIG. 28: Standard curves of platinum drugs with addition of $NaBH_4$. Final: 0-1 μM cisplatin, carboplatin, or oxaliplatin, 20 μM APE, 400 μM TFPP, 5.7 mM $NaBH_4$ 5% DMSO in 1.2 M phosphate pH 7.8 buffer, 25° C., 30 min for cisplatin and carboplatin, 1.5 h for oxaliplatin, n=6.

The addition of NaBH₄ allowed us to successfully detect and quantify all three platinum drugs (FIG. 28). Altogether, these results suggest that we can detect even strongly ligated platinum species by ensuring that the ligands are exchanged for TFPP.

Various aspects of the invention are described in the following numbered clauses:

Clause 1: A method of identifying or quantifying copper in a test sample comprising mixing, thereby producing a reaction mixture:
the test sample;
a triaryl phosphine represented by Formula 1a, optionally dissolved in a solvent,

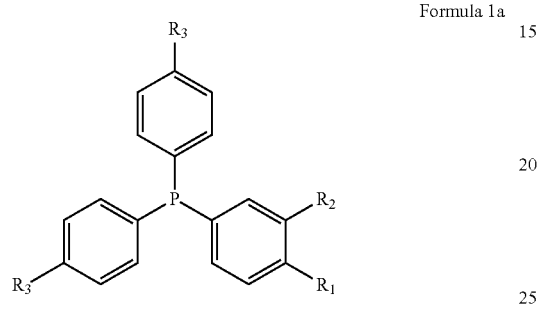

Formula 1a wherein $R_1$ is hydrogen, dialkylamino, $C_{1-6}$ alkyl, fluoro, or $C_{1-6}$ alkoxy; $R_2$ is hydrogen or $SO_3^-$; and $R_3$ is hydrogen, $C_{1-6}$ alkyl, fluoro, amino, or $C_{1-6}$ alkoxy; and a propargyl fluorochrome ether or carbamate, that, when subjected to a depropargylation reaction, results in an increase in fluorescence of the depropargylated fluorochrome as compared to the propargyl fluorochrome at a suitable excitation wavelength of at least 10 times; and reacting the test sample, the triaryl phosphine, and the propargyl fluorochrome ether or carbamate for a time, temperature, and pH sufficient to cause the depropargylation of the propargyl fluorochrome ether or carbamate in the presence of copper in the sample.

Clause 2: The method of clause 1, wherein the copper is $Cu^+$ and/or $Cu^{2+}$.

Clause 3: The method of clause 1, wherein $R_1$ is dimethylamino, $R_2$ is hydrogen, and $R_3$ is hydrogen.

Clause 4: The method of clause 1 or 2, wherein $R_1$ is hydrogen, $R_2$ is $SO_3^-$, and $R_3$ is hydrogen.

Clause 5: The method of clause 1 or 2, wherein $R_1$ is methyl, hydrogen, or methoxy; $R_2$ is hydrogen; and $R_3$ is methyl, hydrogen, or methoxy.

Clause 6: The method of clause 5, wherein $R_1$ and $R_3$ are the same group.

Clause 7: The method of any one of clauses 1, 2, 5, or 6, wherein the triaryl phosphine has at least one ortho- or para-substituent.

Clause 8: The method of any one of clauses 1-7, wherein the triaryl phosphine is dissolved in a solvent, and the solvent comprises N-methylpyrrolidone, dimethylsulfoxide (DMSO), ethanol, or acetonitrile.

Clause 9: The method of any one of clauses 1-8, wherein the reaction mixture has a pH of at least 7.

Clause 10: The method of any one of clauses 1-9, wherein the propargyl fluorochrome ether is propargyl Pittsburgh Green ether (PPE).

Clause 11: The method of any one of clauses 1-10, wherein the reaction mixture comprises:
the test sample;
about 20 μM PPE;
about 150 μM-200 μM triarylphosphine;
about 5-25% ethanol in about 500 mM buffer at a pH of 7-9,
wherein the reaction is performed at from 20° C. to 35° C.

Clause 12: The method of any one of clauses 1-11, wherein the sample is an aqueous or biological sample.

Clause 13: A method of identifying or quantifying platinum in a test sample comprising mixing, thereby producing a reaction mixture:
the test sample;
a triaryl phosphine represented by Formula 1b,

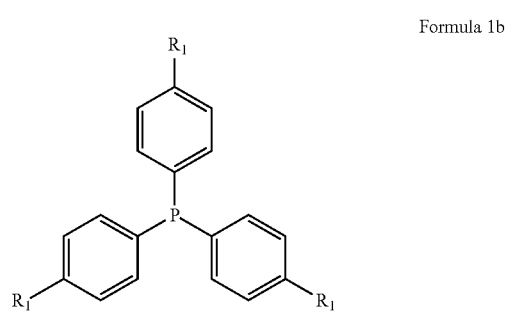

Formula 1b wherein $R_1$ is fluoro, $C_{1-6}$ alkoxy, $C_{1-6}$ alkyl, or hydrogen; or Formula 1c,

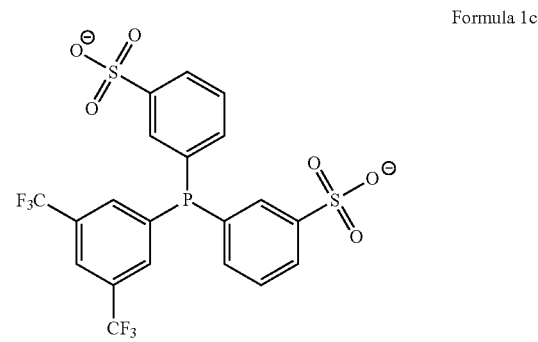 [SMILES: O=S(=O)([O-])c1cccc(P(c2cc(C(F)(F)F)cc(C(F)(F)F)c2)c2cccc(S(=O)(=O)[O-])c2)c1]

Formula 1c optionally dissolved in a solvent; and
an allyl fluorochrome ether or carbamate, that, when subjected to a deallylation reaction, results in an increase in fluorescence of the deallylated fluorochrome ether or carbamate as compared to the allyl fluorochrome ether or carbamate at a suitable excitation wavelength of at least 10 times; and
reacting the test sample, the triaryl phosphine, and the allyl fluorochrome ether or carbamate for a time, temperature, and pH sufficient to cause the allylation of the allyl fluorochrome ether or carbamate in the presence of platinum in the sample.

Clause 14: The method of clause 13, wherein the platinum is Pt(IV), Pt(II), or Pt(0).

Clause 15: The method of clause 13 or 14, wherein the triaryl phosphine is represented by Formula 1b, wherein $R_1$ is fluoro.

Clause 16: The method of clause 13 or 14, wherein the triaryl phosphine is represented by Formula 1b, wherein $R_1$ is hydrogen, methyl, or methoxy.

Clause 17: The method of clause 13 or 14, wherein the triaryl phosphine is represented by Formula 1c.

Clause 18: The method of any one of clauses 13-17, for quantifying cisplatin, oxoplatin, or carboplatin in the test sample.

Clause 19: The method of any one of clauses 13-18, wherein the triaryl phosphine is dissolved in a solvent, and the solvent comprises N-methylpyrrolidone, dimethylsulfoxide (DMSO), ethanol, or acetonitrile.

Clause 20: The method of any one of clauses 13-19, wherein the reaction mixture has a pH of at least 7.

Clause 21: The method of any one of clauses 13-20, wherein the allyl fluorochrome ether is allyl Pittsburgh Green ether (APE).

Clause 22: The method of any one of clauses 13-21, wherein the reaction mixture comprises:
the test sample;
about 20 µM APE;
about 150 µM-200 µM triarylphosphine; and
about 5-25% DMSO in about 1.2 M buffer at a pH of 7-9;
wherein the reaction is performed at from 20° C. to 35° C.

Clause 23: The method of any one of clauses 13-22, wherein the sample is an aqueous or biological sample.

Clause 24: The method of any one of clauses 13-23, further comprising adding a reducing agent to the reaction mixture and reacting the reducing agent with the test sample, the triaryl phosphine, and the allyl fluorochrome ether or carbamate.

Clause 25: A kit for use in identifying or quantifying platinum in a test sample comprising in one or more vessels or containers,
a triaryl phosphine represented by Formula 1b

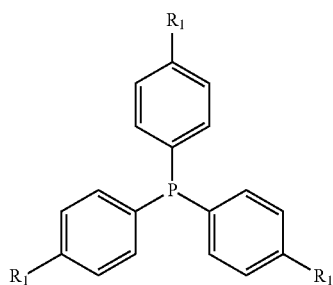

Formula 1b wherein $R_1$ is fluoro, alkoxy, alkyl, or hydrogen; or Formula 1c,

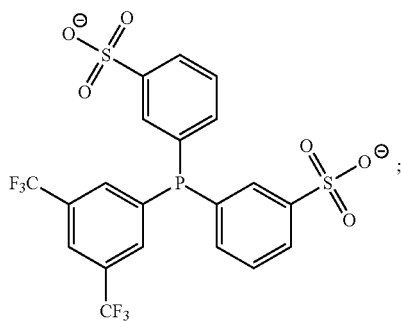

Formula 1c an allyl fluorochrome ether or carbamate, and, optionally, a reducing agent.

Clause 26: The kit of clause 25, wherein the allyl fluorochrome ether or carbamate is allyl Pittsburgh Green ether (APE).

Clause 27: The kit of clause 25 or 26, wherein the reducing agent is present, and the reducing agent is sodium borohydride.

Clause 28: The kit of any one of clauses 25-27, wherein the triaryl phosphine and allyl fluorochrome ether or carbamate are contained in one or more chambers of a cartridge.

Clause 29: A kit for use in identifying or quantifying copper in a test sample comprising in one or more vessels or containers,
a triaryl phosphine represented by Formula 1a,

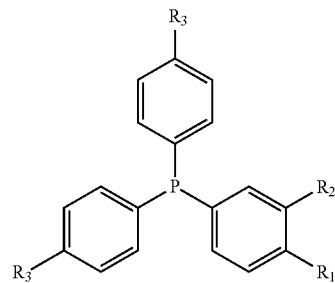

Formula 1a wherein $R_1$ is hydrogen, amino, alkyl, fluoro, or alkoxy,
$R_2$ is hydrogen or $SO_3^-$, and
$R_3$ is hydrogen, alkyl, fluoro, amino, or alkoxy;
a propargyl fluorochrome ether or carbamate,
and, optionally, a reducing agent.

Clause 30: The kit of clause 29, wherein the propargyl ether or carbamate is propargyl Pittsburgh Green ether (PPE).

Clause 31: The kit of clause 29 or 30, wherein the triaryl phosphine and propargyl fluorochrome ether or carbamate are contained in one or more chambers of a cartridge.

Having described this invention, it will be understood to those of ordinary skill in the art that the same can be performed within a wide and equivalent range of conditions, formulations and other parameters without affecting the scope of the invention or any embodiment thereof.

What is claimed is:

1. A method of identifying or quantifying copper in a test sample comprising:
mixing, thereby producing a reaction mixture:
the test sample;
a triaryl phosphine represented by Formula 1a, optionally dissolved in a solvent,

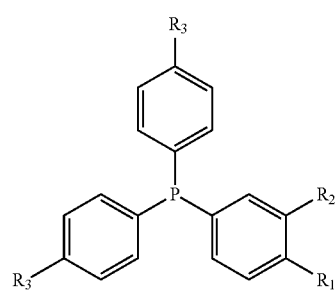

Formula 1a wherein $R_1$ is hydrogen, dialkylamino, $C_{1-6}$ alkyl, fluoro, or $C_{1-6}$ alkoxy; $R_2$ is hydrogen or $SO_3^-$; and $R_3$ is hydrogen, $C_{1-6}$ alkyl, fluoro, amino, or $C_{1-6}$ alkoxy; and a propargyl fluorochrome ether or carbamate, that, when subjected to a depropargylation reaction to produce a depropargylated fluorochrome, results in an increase in fluorescence of the depropargylated fluorochrome as compared to the propargyl fluorochrome of at least 10 times at a fluorescence excitation wavelength of the depropargylated fluorochrome;

reacting the test sample, the triaryl phosphine, and the propargyl fluorochrome ether or carbamate for a time, temperature, and pH sufficient to cause the depropargylation of the propargyl fluorochrome ether or carbamate in presence of copper in the sample; and identifying or quantifying copper in the test sample by determining or quantifying fluorescence of the reaction mixture when illuminated at the excitation wavelength of the depropargylated fluorochrome.

2. The method of claim 1, wherein the copper is $Cu^+$ and/or $Cu^{2+}$.

3. The method of claim 1, wherein:
$R_1$ is dimethylamino, $R_2$ is hydrogen, and $R_3$ is hydrogen;
$R_1$ is hydrogen, $R_2$ is $SO_3^-$, and $R_3$ is hydrogen, or
$R_1$ is methyl, hydrogen, or methoxy; $R_2$ is hydrogen; and $R_3$ is methyl, hydrogen, or methoxy.

4. The method of claim 3, wherein $R_1$ is methyl, hydrogen, or methoxy; $R_2$ is hydrogen; and $R_3$ is methyl, hydrogen, or methoxy and wherein $R_1$ and $R_3$ are the same.

5. The method of claim 1, wherein the triaryl phosphine has at least one ortho- or para-substituent.

6. The method of claim 1, wherein the reaction mixture has a pH of at least 7.

7. The method of claim 1, wherein the propargyl fluorochrome ether is propargyl Pittsburgh Green ether (PPE).

8. The method of claim 1, wherein the reaction mixture comprises:
the test sample;
about 20 µM propargyl fluorochrome ether comprising propargyl Pittsburgh Green ether;
about 150 µM-200 µM triarylphosphine;
about 5-25% ethanol in about 500 mM buffer at a pH of 7-9,
wherein the reaction is performed at from 20° C. to 35° C.

9. The method of claim 1, wherein the sample is an aqueous or biological sample.

10. A kit for use in identifying or quantifying copper in a test sample comprising in one or more vessels or containers:
a triaryl phosphine represented by Formula 1a,

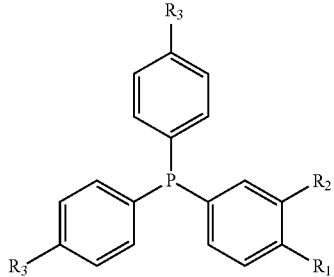

Formula 1a wherein $R_1$ is hydrogen, amino, alkyl, fluoro, or alkoxy, $R_2$ is hydrogen or $SO_3^-$, and $R_3$ is hydrogen, alkyl, fluoro, amino, or alkoxy;
a propargyl fluorochrome ether or carbamate,
and, optionally, a reducing agent.

11. The kit of claim 10, wherein the triaryl phosphine and propargyl fluorochrome ether or carbamate are contained in one or more chambers of a cartridge.

12. The kit of claim 10, wherein the propargyl fluorochrome ether is propargyl Pittsburgh Green ether.

* * * * *

UNITED STATES PATENT AND TRADEMARK OFFICE
CERTIFICATE OF CORRECTION

PATENT NO. : 11,340,164 B2
APPLICATION NO. : 16/381504
DATED : May 24, 2022
INVENTOR(S) : Kazunori Koide et al.

It is certified that error appears in the above-identified patent and that said Letters Patent is hereby corrected as shown below:

In the Claims

Column 27, Line 38, Claim 7, delete "ether (PPE)" and insert -- ether. --

Signed and Sealed this
Twentieth Day of September, 2022

Katherine Kelly Vidal
*Director of the United States Patent and Trademark Office*